(12) United States Patent
Tao et al.

(10) Patent No.: US 7,799,954 B2
(45) Date of Patent: Sep. 21, 2010

(54) DICARBONYL DERIVATIVES AND METHODS OF USE

(75) Inventors: Chunlin Tao, Los Angeles, CA (US); Qinwei Wang, Alhambra, CA (US); Vuong Trieu, Calabasas, CA (US); Neil Desai, Los Angeles, CA (US); Patrick Soon-Shiong, Los Angeles, CA (US)

(73) Assignee: Abraxis BioScience, LLC, Los Angeles, CA (US)

( * ) Notice: Subject to any disclaimer, the term of this patent is extended or adjusted under 35 U.S.C. 154(b) by 489 days.

(21) Appl. No.: 11/939,909

(22) Filed: Nov. 14, 2007

(65) Prior Publication Data

US 2008/0146586 A1 Jun. 19, 2008

Related U.S. Application Data

(60) Provisional application No. 60/866,341, filed on Nov. 17, 2006.

(51) Int. Cl.
*C07C 49/15* (2006.01)
*A61K 31/12* (2006.01)

(52) U.S. Cl. ............ 568/329; 514/252.12; 514/252.13; 514/354; 514/408; 514/465; 514/475; 514/545; 514/568; 514/621; 514/679; 544/386; 546/328; 548/570; 549/434; 549/512; 560/51; 562/459; 564/169; 568/331; 568/335; 568/417

(58) Field of Classification Search ............ 514/252.12, 514/252.13, 354, 408, 465, 475, 545, 568, 514/621, 679, 690; 544/386; 546/328; 548/570; 549/434, 512; 560/51; 562/459; 564/169; 568/329, 331, 335, 417
See application file for complete search history.

(56) References Cited

U.S. PATENT DOCUMENTS

| 4,130,661 | A | 12/1978 | Kulsa et al. |
|---|---|---|---|
| 5,068,393 | A | 11/1991 | Maignan et al. |
| 5,618,829 | A | 4/1997 | Takayanagi et al. |
| 5,916,596 | A | 6/1999 | Desai et al. |
| 6,506,405 | B1 | 1/2003 | Desai et al. |
| 6,537,579 | B1 | 3/2003 | Desai et al. |
| 2007/0155816 | A1 | 7/2007 | Kim et al. |

FOREIGN PATENT DOCUMENTS

| EP | 0 608 897 A2 | 8/1994 |
|---|---|---|
| WO | WO 97/22596 A1 | 6/1997 |
| WO | WO 97/30035 A1 | 8/1997 |
| WO | WO 97/32856 A1 | 9/1997 |
| WO | WO 98/13354 A1 | 4/1998 |
| WO | WO 2004/072051 A1 | 8/2004 |
| WO | WO 2005/070416 A1 | 8/2005 |

OTHER PUBLICATIONS

Dessau et al., *J. Org. Chem.*, 39 (23), 3457-3459 (1974).
Frazier, Jr. et al., *J. Org. Chem.*, 45, 5408-5411 (1980).
Hansen et al., *J. Org. Chem.*, 70, 7761-7764 (2005).
He et al., *J. Am. Chem. Soc.*, 123, 5362-5363 (2001).
Himo et al., *J. Am. Chem. Soc.*, 127, 210-216 (2005).
Ikuina et al., *J. Med. Chem.*, 46, 2534-2541 (2003).
Ito et al., *J. Am. Chem. Soc.*, 97, 649-651 (Feb. 5, 1975).
Ito et al., *J. Am. Chem. Soc.*, 99, 1487-1493 (Mar. 2, 1977).
Paquette et al., *J. Org. Chem.*, 60, 7277-7283 (1995).
Parhi et al., *Organic Lett.*, 6 (18), 3063-3065 (2004).
Rathke et al., *J. Am. Chem. Soc.*, 93, 4605-4606 (Sep. 8, 1971).
Backvall et al., *Tetrahedron Letters*, 32(40): 5607-5610 (1991).
Echavarren et al., *J. Org. Chem.*, 59(15): 4179-4185 (1994).
Enders et al., *Synlett*, Institut fur Organische Chemie: 43-44 (Jan. 1998).
Jacobson et al., *J. Org. Chem.*, 42(15): (1977).
Ji et al., "Antineoplastic effect of indirubin derivatives and their structure-activity relations," *Yaoxue Xuebao*, 20(2): 137-139 (1985).
Wiley et al., *Journal of Chemical Engineering Data*, 10(1): 72-73 (Jan. 1965).

*Primary Examiner*—Shailendra Kumar
(74) *Attorney, Agent, or Firm*—Leydig, Voit & Mayer, Ltd.

(57) ABSTRACT

Derivatives of dicarbonyl compounds having antitumor and antibiotic activity which can be used as anticancer agents.

60 Claims, No Drawings

DICARBONYL DERIVATIVES AND METHODS OF USE

CROSS-REFERENCE TO RELATED APPLICATIONS

This patent application claims the benefit of U.S. Provisional Patent Application No. 60/866,341, filed Nov. 17, 2006, which is incorporated by reference.

The present invention relates to the derivatives of dicarbonyl compounds having antitumor and antibiotic activity which can be used as anticancer agents.

BACKGROUND OF THE INVENTION

It has been reported that novel natural products Lomaiviticins A and B, isolated from the actinomycete *Micromonospora lomaivitiensis*, are potent antitumor and antibiotic agents (He, H. et al., *J. Am. Chem. Soc.* 2001, 123, 5362-5363). These lomaiviticins are potent DNA cleaving agents with in vitro cytotoxicity against a number of cell lines with $IC_{50}$ values ranging from 0.01 to 98 ng/mL. Inspection of the structures of the lomaiviticins leads to the recognition of the following structural elements: (a) the diazo groups; (b) the tetracyclic framework of the monomeric unit; (c) the carbohydrate moieties; (d) the hindered central carbon-carbon bond linking the two units; (e) the readily labile β-alkoxy functionality at C-3 and C-3' and (f) the dicarbonyl core structure in lomaivitivin A.

On the other hand, patents revealed that benzoylacrylamide derivatives, containing dicarbony group, have intensive tyrosine kinase inhibiting activity and can be used as anticancer agents (U.S. Pat. Nos. 5,618,829; 4,130,661; EP Patent Application No. 0608897A2). It is well known that tyrosine kinase plays an important role in intercellular signal transduction and cell differentiation or growth. Accordingly, failure of control of tyrosine kinase activity in cells disorders intercellular signal transduction and causes abnormal cell differentiation/growth, which is considered to be directly responsible for the development of various diseases. In particular, it is known that tyrosine kinase is significantly associated with disorderly overgrowth of cancer cells. It has been proposed that an agent specifically inhibiting tyrosine kinase activity would be an anti-cancer agent having minor side-effects and exerting its therapeutic effect through novel mechanisms.

The recognitions of the dicarbonyl group in the novel natural product lomaiviticin A as one of the core structures to exert its anticancer activity, together with the novel tyrosine kinase inhibitory activity of benzoylacrylamide derivatives, lead inventors of the present invention to devote them to a study for developing a new class of dicarbonyl derivatives. Accordingly, the purpose of the present invention is to provide a family of novel compounds useful for suppressing the growth of cancer cells, which compounds are easily available, exhibit specific and intensive activity in inhibiting tyrosine kinase of the growth factor receptor, and show negligible side-effects compared with previously known anti-cancer agents.

Several reports have disclosed the preparation of some dicarbonyl derivatives. The synthesis of 1,4-diketones have been disclosed in the publication by (a) Rathke, M. W. et al (*J. Am. Chem. Soc.* 1971, 93, 4605-4606); (b) Dessau, R. M et al (*J. Org. Chem.* 1974, 39, 3457-3459); (c) Ito, Y. et al (*J. Am. Chem. Soc.* 1975, 97, 2912-2914); (d) Ito, Y. et al (*J. Am. Chem. Soc.* 1977, 99, 1487-1493); (e) Frazier, R. H et al (*J. Org. Chem.* 1980, 45, 5408-5411); (f) Paquette, L. A. et al (*J. Org. Chem.* 1995, 60, 7277-7283). For example, [4,4'-bycyclohexenyl]-3,3'-dione can be prepared from 2-cyclohexene-1-one, which was converted to its enolate with LDA and oxidized with ferric chloride (*J. Org. Chem.* 1980, 45, 5408-5411). Copper chloride and silver oxide have also been used as the oxidative reagents (*J. Am. Chem. Soc.* 1977, 99, 1487-1493; *J. Am. Chem. Soc.* 1975, 97, 649). The syntheses of benzoylacrylamide derivatives have been disclosed in patents (U.S. Pat. Nos. 5,618,829; 4,130,661; EP Patent Application No. 0608897A2). For example, 3,4-dimethoxyacetophenone reacted with glyoxylic acid monohydrate under reflux provided the corresponding substituted benzoylacrylic acid, which can be converted to various amides (U.S. Pat. No. 5,618,829). The synthesis of oxime, such as oxime derivatives of radicicol, was reported for their preparation (Ikuina, Y. et al, *J. Med. Chem.* 2003, 46, 2534-2541). The preparation of isoxazoles were also revealed (Hansen, T. V. et al, *J. Org. Chem.* 2005, 70, 7761-7764; PArHi, A. K. et al, *Org. Lett.* 2004, 6, 3063-3065; Himo, F. et al, *J. Am. Chem. Soc.* 2005, 127, 210-216; WO 2004/072051 A1).

SUMMARY OF THE INVENTION

Accordingly, it is an objective of the present invention to provide an antitumor agent comprising a dicarbonyl derivative as described in formula (I), pharmaceutically-acceptable formulations thereof, and methods for using such derivatives (alone and in combination with other therapeutic agents) against different types of tumors. The combination therapy described herein may be provided by the preparation of the dicarbonyl derivative of formula (I) and the other therapeutic agent as separate pharmaceutical formulations followed by the administration thereof to a patient simultaneously, semi-simultaneously, separately or over regular intervals.

Additional objects and advantages of the present invention will be set forth in part in the description which follows, and in part will be apparent from the description, or may be learned by practice of the present invention.

DETAILED DESCRIPTION OF THE INVENTION

The compounds of the present invention are those dicarbonyl derivatives of formula

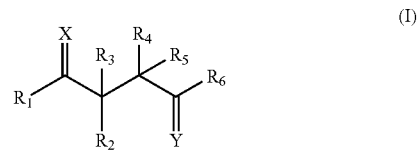

(I)

wherein:

$R_1$, $R_2$, $R_3$, $R_4$, $R_5$, and $R_6$ are independently: a hydrogen atom or an alkyl, alkoxy, alkylthiol, alkylamino, alkenyl, alkynyl group comprising 1 to 30 carbon atoms and which is unsubstituted or substituted by at least one of the substituents (a) as defined below;

an aryl group comprising 6 to 14 ring atoms and which is unsubstituted or substituted by at least one of the substituents (b) as defined below;

a heterocyclic group which has 5 or 6 ring atoms of which from 1 to 3 are nitrogen and/or oxygen and/or sulphur heteroatoms, said heterocyclic group being unsubstituted or substituted by at least one of the substituents (c) as defined below;

X and Y are O, NR' or S; and $R^1$ represents a group of substituents (a) as defined below; wherein substituent (a) is a hydroxy group, an alkoxy group comprising from 1 to 20 carbon atoms and which are unsubstituted or substituted by at least one alkoxy group comprising from 1 to 4 carbon atoms and/or an alkylthio group comprising from 1 to 4 carbon atoms; an aryl group comprising from 6 to 14 ring atoms and which are unsubstituted or substituted by at least one of the substituents (b) as defined below; or a group of formula —NR$^1$R$^2$, —CONR$^1$R$^2$, —OR$^1$ or —OCON R$^1$R$^2$, wherein R$^1$ and R$^2$ are the same or different and are a hydrogen atom; an alkyl, alkoxy, alkenyl, or alkynyl group comprising from 1 to 20 carbon atoms, which group is unsubstituted or substituted by at least one of substituents (b) other than the group of formula —NR$^1$R$^2$, —CONR$^1$R$^2$, —OR$^1$ and —OCON R$^1$R$^2$ or by an aryl group in which the aryl moiety comprises 6 to 10 ring carbon atoms and is unsubstituted or substituted by at least one of the substituents (b) as defined below; or a heterocyclic group being unsubstituted or substituted by at least one of the substituents (c) as defined below;

wherein substituent (b) is a hydroxy group; a cyano group; a mercapto group; a halogen atom; an alkyl group comprising from 1 to 8 carbon atoms;

a group of formula —NR$^1$R$^2$, —CONR$^1$R$^2$ or —OCON R$^1$R$^2$, wherein R$^1$ and R$^2$ are as defined above;

an alkylthio group comprising 1 to 20 carbon atoms;

a heterocyclic group comprising 5 or 6 ring atoms of which from 1 to 3 are nitrogen and/or oxygen and/or sulphur heteroatoms, said heterocyclic group being unsubstituted or substituted by at least one of the substituents (c) as defined below; and wherein substituent (c) is a hydroxy group; a halogen atom, a cyano group; an alkyl group comprising 1 to 8 carbon atoms; an aryl group comprising 6 to 10 ring atoms and which are unsubstituted or substituted by at least one of the substituents (b) as defined above;

a group of formula —NR$^1$R$^2$, —CONR$^1$R$^2$ or —OCON R$^1$R$^2$, wherein R$^1$ and R$^2$ are as defined above;

an aryl group in which the aryl moiety comprises 6 to 10 ring carbon atoms and is unsubstituted or substituted by at least one of the substituents (b) as defined above;

an aliphatic carboxylic acyl group comprising 1 to 20 carbon atoms;

an aromatic carboxylic acyl group in which the aryl moiety comprises 6 to 10 ring carbon atoms and is unsubstituted or substituted by at least one of the substituents (b) as defined above.

The present invention also provides, in a preferred embodiment, a compound or pharmaceutically acceptable salt thereof having the formula (I)

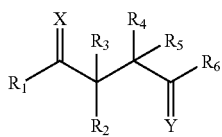

(I)

wherein

R$_1$, R$_2$, R$_3$, R$_4$, R$_5$, and R$_6$ are independently a hydrogen atom or an alkyl, alkenyl, alkynyl, or aryl comprising 1 to 30 carbon atoms and which is unsubstituted or substituted by at least one of hydroxy, cyano, mercapto, halogen, —OR$_7$, SR$_7$, —NR$_7$R$_8$, —CONR$_7$R$_8$, or —OCONR$_7$R$_8$, wherein R$_7$ and R$_8$ are independently a hydrogen atom; an alkyl, alkenyl, or alkynyl comprising 1 to 20 carbon atoms; a cyclic or heterocyclic group comprising 5 or 6 ring atoms of which from 0 to 3 are nitrogen and/or oxygen and/or sulphur hetero-atoms, said cyclic or heterocyclic group being unsubstituted or substituted by at least one of hydroxy, cyano, mercapto, halogen, or an alkyl group comprising 1 to 6 carbon atoms; and X and Y are respectively O, NR$_7$ or S, wherein when X and Y are O, and if R$_2$, R$_4$ are hydrogen, R$_1$-R$_3$ or both R$_1$-R$_3$ and R$_5$-R$_6$ form a cyclic or an acyclic alkenyl; and when X and Y are O, and if R$_2$, R$_4$ form a single bond, R$_1$ is

wherein Ar is an aryl or heteroaryl.

The following definitions refer to the various terms used above and throughout the disclosure.

The term "halogen" refers to fluoro, chloro, bromo or iodoi atom.

The term "alkyl" refers to an alkyl, substituted or unsubstituted, straight or branched chain group, having from 1-30 carbon atoms. Illustrative of the alkyl group include the methyl, ethyl, propyl, isopropyl, butyl, isobutyl, sec-butyl, t-butyl, pentyl, 3-methylbutyl, 2,2-dimethylpropyl, 1,1-dimethylpropyl, hexyl, 1-methylpentyl, 4-methylpentyl, heptyl, 1-methylhexyl, 2-methylhexyl, 5-methylhexyl, 3-ethylpentyl, octyl, 2-methylheptyl, 6-methylheptyl, 2-ethylhexyl, 2-ethyl-3-methylpentyl, 3-ethyl-2-methylpentyl, nonyl, 2-methyloctyl, 7-methyloctyl, 4-ethylheptyl, 3-ethyl-2-methylhexyl, 2-ethyl-1-methylhexyl, decyl, 2-methylnonyl, 8-methylnonyl, 5-ethyloctyl, 3-ethyl-2-methylheptyl, 3,3-diethylhexyl, undecyl, 2-methyldecyl, 9-methyldecyl, 4-ethylnonyl, 3,5-dimethylnonyl, 3-propyloctyl, 5-ethyl-4-methyloctyl, 1-pentylhexyl, dodecyl, 1-methylundecyl, 10-methylundecyl, 3-ethyldecyl, 5-propylnonyl, 3,5-diethyloctyl, tridecyl, 11-methyldodecyl, 7-ethylundecyl, 4-propyldecyl, 5-ethyl-3-methyldecyl, 3-pentyloctyl, tetradecyl, 12-methyltridecyl, 8-ethyldodecyl, 6-propylundecyl, 4-butyldecyl, 2-pentylnonyl, pentadecyl, 13-methyltetradecyl, 10-ethyltridecyl, 7-propyldodecyl, 5-ethyl-3-methyldodecyl, 4-pentyldecyl, 1-hexylnonyl, hexadecyl, 14-methylpentadecyl, 6-ethyltetradecyl, 4-propyltridecyl, 2-butyldodecyl, heptadecyl, 15-methylhexadecyl, 7-ethylpentadecyl, 3-propyltetradecyl, 5-pentyldodecyl, octadecyl, 16-methylheptadecyl, 5-propylpentadecyl, nonadecyl, 17-methyloctadecyl, 4-ethylheptadecyl, icosyl, 18-methylnonadecyl, 3-ethyloctadecyl, henicosyl, docosinyl, tricosinyl, tetracosinyl and pentacosinyl groups.

The term "alkenyl" represents an alkenyl group having from 2 to 30 carbon atoms and may be a straight or branched chain group. It may have 1 or more, preferably from 2 to 6, double bonds. Examples of such groups include the vinyl, allyl, 1-propenyl, isopropenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 1-octenyl, 8-nonenyl, 1-nonenyl, 1-decenyl, 9-decenyl, 8-tridecenyl, cis-8-pentadecenyl, trans-8-pentadecenyl, 8-heptadecenyl, 8-heptadecenyl, 8,11-heptadecadienyl, 8,11,14-heptadecatrienyl, 4,7,11,14-nonadecatetraenyl and 2,6-dimethyl-8-(2,6,6-trimethyl-1-cyclohexen-1-yl)-1,3,5,7-nonatetraen-1-yl, cis-10-nonadecaenyl, 10,13-nonadecadienyl, cis-7,10,13-nonadecatrienyl, 5,8,11,14-nonadecatetraenyl, nonadecapentaenyl.

The term "alkoxy" refers to an alkoxy group with 1 to 20 carbon alkyl groups, and the alkyl moiety thereof generally corresponds to the $C_1$-$C_{20}$ alkyl groups described above and can be selected wherefrom. Examples of such groups include the methoxy, ethoxy, propoxy, isopropoxy, butoxy, isobutoxy, sec-butoxy, t-butoxy, pentoxy, 3-methylbutoxy, 2,2-dimethylpropoxy, 1,1-dimethylpropoxy, hexyloxy, 1-methylpentyloxy, 4-methylpentyloxy, heptyloxy, 1-methylhexyloxy, 2-methylhexyloxy, 5-methylhexyloxy, 3-ethylpentyloxy, octyloxy, 2-methylheptyloxy, 6-methylheptyloxy, 2-ethylhexyloxy, 2-ethyl-3-methylpentyloxy, 3-ethyl-2-methylpentyloxy, nonyloxy, 2-methyloctyloxy, 7-methyloctyloxy, 4-ethylheptyloxy, 3-ethyl-2-methylhexyloxy, 2-ethyl-1-methylhexyloxy, decyloxy, 2-methylnonyloxy, 8-methylnonyloxy, 5-ethyloctyloxy, 3-ethyl-2-methylheptyloxy, 3,3-diethylhexyloxy, undecyloxy, 2-methyldecyloxy, 9-methyldecyloxy, 4-ethylnonyloxy, 3,5-dimethylnonyloxy, 3-propyloctyloxy, 5-ethyl-4-methyloctyloxy, 1-pentylhexyloxy, dodecyloxy, 1-methylundecyloxy, 10-methylundecyloxy, 3-ethyldecyloxy, 5-propylnonyloxy, 3,5-diethyloctyloxy, tridecyloxy, 11-methyldodecyloxy, 7-ethylundecyloxy, 4-propyldecyloxy, 5-ethyl-3-methyldecyloxy, 3-pentyloctyloxy, tetradecyloxy, 12-methyltlidecyloxy, 8-ethyldodecyloxy, 6-propylundecyloxy, 4-butyldecyloxy, 2-pentylnonyloxy, pentadecyloxy, 13-methyltetradecyloxy, 10-ethyltridecyloxy, 7-propyldodecyloxy, 5-ethyl-3-methyldodecyloxy, 4-pentyldecyloxy, 1-hexylnonyloxy, hexadecyloxy, 14-methylpentadecyloxy, 6-ethyltetradecyloxy, 4-propyltridecyloxy, 2-butyldodecyloxy, heptadecyloxy, 15-methylhexadecyloxy, 7-ethylpentadecyloxy, 3-propyltetradecyloxy, 5-pentyldodecyloxy, octadecyloxy, 16-methylheptadecyloxy, 5-propylpentadecyloxy, nonadecyloxy, 17-methyloctadecyloxy, 4-ethylheptadecyloxy, icosyloxy, 18-methylnonadecyloxy, and 3-ethyloctadecyloxy groups.

The term "aryl" and "heterocyclic" refers to an aromatic or heteroaromatic ring. The aryl ring can be substituted with substituents selected from the group consisting of halogen, $C_1$-$C_6$ alkyl or $C_1$-$C_6$ alkoxy, or alkyl amino. Examples include 4-chlorophenyl, 2-fluorophenyl, 4-fluorophenyl, 3-fluorophenyl, 4-methylphenyl, 4-ditrifluorohenyl, 2-ethylphenyl, 3-n-propylphenyl, 4-isopropyl-phenyl, 4-n-butylphenyl, 4-t-butylphenyl, 4-sec-butylphenyl, 4-dimethylaminophenyl, 3,4-dimethylphenyl, 4-methoxyphenyl, 4-ethoxyphenyl, 4-isopropoxyphenyl, 3-isobutoxyphenyl, 4-t-butoxyphenyl, 4-nitrophenyl, 2-furan, 2-pyridyl, 3-pyridyl, 2-thiophenyl, 3-thiophenyl, 1-naphthyl, 2-naphthyl, 2-indolyl, and the like, and the aryl moiety of aryl and arylcarbamoyl have the same meaning. Examples of the heterocyclic group include the furyl, thienyl, pyrrolyl, pyridyl, thiazolyl, isothiazolyl, oxazolyl, isoxazolyl, imidazolyl, pyrazolyl, pyranyl, pyrazinyl, pyridazinyl, pyrimidinyl, tetrahydrofuranyl, tetrahydrothienyl, pyrrolidinyl, thiazolidinyl, thiazolinyl, isothiazolinyl, imidazolidinyl, imidazolinyl, oxazolinyl, isoxazolinyl, oxazolidinyl, pyrazolidinyl, piperazinyl, dioxopiperazinyl, tetrahydropyrimidinyl, dihydropyridazinyl, morpholinyl, thiomorpholinyl, pyrrolidonyl, piperidonyl, pyridonyl, 2H-pyrrolyl, furazanyl and pyrazolinyl groups, especially the furyl, pyrrolyl, pyridyl, thiazolyl, isothiazolyl, oxazolyl, isoxazolyl, imidazolyl, pyridazinyl, pyrrolidinyl, thiazolinyl, isothiazolinyl, imidazolyl, piperazinyl, dioxopiperazinyl, morpholinyl, pyrrolidonyl and piperidonyl groups. Such groups may be unsubstituted or they may be substituted by at least one of substituents (c), defined above and exemplified below.

The term "alkylamino" refers to a substituted derivative of ammonia, wherein one or two hydrogen of ammonia is replaced by an alkyl group having 1 to 20 carbon, and the alkyl moiety thereof generally corresponds to the $C_1$-$C_{20}$ alkyl groups described above and can be selected wherefrom. Examples of the alkylamino include the are methylamino, ethylamino, propylamino, 1-methylethylamino, butylamino, isobutylamino, sec-butylamino, t-butylamino, pentylamino, 3-methylbutylamino, 2,2-dimethylpropylamino, 1,1-dimethylpropylamino, hexylamino, 1-methylpentylamino, 4-methylpentylamino, heptylamino, 1-methylhexylamino, 2-methylhexylamino, 5-methylhexylamino, 3-ethylpentylamino, octylamino, 2-methylheptylamino, 6-methylheptylamino, 2-ethylhexylamino, 2-ethyl-3-methylpentylamino, 3-ethyl-2-methylpentylamino, nonylamino, N,N-dimethylamino, N,N-diethylamino, N,N-dipropylamino, N-methyl-N-ethylamino, N,N-dibutylamino, N-methyl-N-(1,1-dimethylethyl) amino, and like.

The term "alkylthio" refers to a thio group with 1 to 20 carbon alkyl groups, and the alkyl moiety thereof generally corresponds to the $C_1$-$C_{20}$ alkyl groups described above and can be selected wherefrom. Examples include the methylthio, ethylthio, propylthio, isopropylthio, butylthio, isobutylthio, sec-butylthio, t-butylthio, pentylthio, 3-methylbutylthio, 2,2-dimethylpropylthio, 1,1-dimethylpropylthio, hexylthio, 1-methylpentylthio, 4-methylpentylthio, heptylthio, 1-methylhexylthio, 2-methylhexylthio, 5-methylhexylthio, 3-ethylpentylthio, octylthio, 2-methylheptylthio, 6-methylheptylthio, 2-ethylhexylthio, 2-ethyl-3-methylpentylthio, 3-ethyl-2-methylpentylthio, nonylthio, 2-methyloctylthio, 7-methyloctylthio, 4-ethylheptylthio, 3-ethyl-2-methylhexylthio, 2-ethyl-1-methylhexylthio, decylthio, 1-pentylhexylthio, dodecylthio, octadecylthio, 16-methylheptadecylthio, nonadecylthio, 18-methylnonadecylthio and 3-ethyloctadecylthio groups;

The term "cycloalkyl" refers to alkyl group that has from 3 to 8 carbon atoms and may be unsubstituted or substituted. If it is substituted, it is substituted by at least one of substituents (c), defined above and exemplified below. Examples of such groups include the cyclopropyl, cyclobutyl, cyclopentyl, cyclohexyl, cyclopentyl and cyclooctyl groups and substituted analogues thereof.

The term "cycloalkenyl" refers to a group that has from has from 5 to 8 carbon atoms and may be unsubstituted or substituted. If it is substituted, it is substituted by at least one of substituents (c), defined above and exemplified below. It has one or more, preferably 1 or 2, more preferably 1, carbon-carbon double bond or bonds. Examples of such groups include the 1-cyclopenten-1-yl, 2-cyclopenten-1-yl, 1-cyclohexen-1-yl, 2-cyclohexen-1-yl, 3-cyclohexen-1-yl, 1-cylohepten-1-yl, 2-cyclohepten-1-yl, 1-cycloocten-1-yl and 3-cyclocten-1-yl groups and substituted analogues thereof.

The term "pharmaceutically acceptable salts" of the compounds of the invention include those derived from pharmaceutically acceptable inorganic and organic acids and bases. Examples of suitable acids include hydrochloric, hydrobromic, sulfuric, nitric, perchloric, fumaric, maleic, phosphoric, glycolic, gluconic, lactic, salicylic, succinic, toluene-p 10 sulfonic, tartaric, acetic, citric, methanesulfonic, formic, benzoic, malonic, naphthalene-2-sulfonic, benzenesulfonic, 1,2 ethanesulfonic acid (edisylate), galactosyl-d-gluconic acid, and the like. Other acids, such as oxalic acid, while not themselves pharmaceutically acceptable, may be employed in the preparation of salts useful as intermediates in obtaining the compounds of this invention and their pharmaceutically acceptable acid 15 addition salts. Salts derived from appropriate bases include alkali metal (e.g. sodium), alkaline earth metal (e.g. magnesium), ammonium and N—($C_1$-$C_4$ alkyl)$_4^+$ salts, and the like. Illustrative examples of some of these include sodium hydroxide, potassium hydroxide, choline hydroxide, sodium carbonate, and the like.

A number of compounds of formula I possess asymmetric carbons and can therefore exist in racemic and optically active forms. Methods of separation of enantiomeric and diastereomeric mixtures are well known to one skilled in the art. The present invention encompasses any isolated racemic or optically active form of compounds described in formula I, and uses thereof as described herein.

Examples of groups and atoms which may be included in substituents (a) are: hydroxy groups; chlorine, fluorine, bromine and iodine atoms; cyano group; mercapto groups; carboxy groups; alkoxy groups which have from 1 to 20 carbon atoms and which are unsubstituted or are substituted by at least one alkoxy group having from 1 to 4 carbon atoms and/or alkylthio group having from 1 to 4 carbon atoms, such as the methoxy, ethoxy, propoxy, isopropoxy, butoxy, isobutoxy, sec-butoxy, t-butoxy, pentyloxy, methoxymethoxy, 1-methoxyethoxy, 2-methoxyethoxy, butoxymethoxy, 2-butoxyethoxy, 3-ethoxypropoxy, 3-methylbutoxy, 2,2-dimethylpropoxy, 1,1-dimethylpropoxy, hexyloxy, 1-methylpentyloxy, 4-methylpentyloxy, heptyloxy, 1-methylhexyloxy, 2-methylhexyloxy, 5-methylhexyloxy, 3-ethylpentyloxy, octyloxy, 2-methylheptyloxy, 6-methylheptyloxy, 2-ethylhexyloxy, 2-ethyl-3-methylpentyloxy, 3-ethyl-2-methylpentyloxy, nonyloxy, 2-methyloctyloxy, 7-methyloctyloxy, 4-ethylheptyloxy, 3-ethyl-2-methylhexyloxy, 2-ethyl-1-methylhexyloxy, decyloxy, 2-methylnonyloxy, 8-methylnonyloxy, 5-ethyloctyloxy, 3-ethyl-2-methylheptyloxy, 3,3-diethylhexyloxy, undecyloxy, 2-methyldecyloxy, 9-methyldecyloxy, 4-ethylnonyloxy, 3,5-dimethylnonyloxy, 3-propyloctyloxy, 5-ethyl-4-methyloctyloxy, 1-pentylhexyloxy, dodecyloxy, 1-methylundecyloxy, 10-methylundecyloxy, 3-ethyldecyloxy, 5-propylnonyloxy, 3,5-diethyloctyloxy, tridecyloxy, 11-methyldodecyloxy, 7-ethylundecyloxy, 4-propyldecyloxy, 5-ethyl-3-methyldecyloxy, 3-pentyloctyloxy, tetradecyloxy, 12-methyltridecyloxy, 8-ethyldodecyloxy, 6-propylundecyloxy, 4-butyldecyloxy, 2-pentylnonyloxy, pentadecyloxy, 13-methyltetradecyloxy, 10-ethyltlidecyloxy, 7-propyldodecyloxy, 5-ethyl-3-methyldodecyloxy, 4-pentyldecyloxy, 1-hexylnonyloxy, hexadecyloxy, 14-methylpentadecyloxy, 6-ethyltetradecyloxy, 4-propyltridecyloxy, 2-butyldodecyloxy, heptadecyloxy, 15-methylhexadecyloxy, 7-ethylpentadecyloxy, 3-propyltetradecyloxy, 5-pentyldodecyloxy, octadecyloxy, 16-methylheptadecyloxy, 5-propylpentadecyloxy, nonadecyloxy, 17-methyloctadecyloxy, 4-ethylheptadecyloxy, icosyloxy and 18-methylnonadecyloxy, 3-ethyloctadecyloxy groups; aryl groups which have from 6 to 14 ring atoms and which are unsubstituted or which are substituted by at least one of substituents (b), defined above and exemplified below, such as the phenyl, 1-naphthyl, 2-naphthyl, fluorenyl, 1-anthryl and 1-phenanthryl groups and substituted analogues thereof;

alkylthio groups having from 1 to 20 carbon atoms, such as the methylthio, ethylthio, propylthio, isopropylthio, butylthio, isobutylthio, sec-butylthio, t-butylthio, pentylthio, 3-methylbutylthio, 2,2-dimethylpropylthio, 1,1-dimethylpropylthio, hexylthio, 1-methylpentylthio, 4-methylpentylthio, heptylthio, 1-methylhexylthio, 2-methylhexylthio, 5-methylhexylthio, 3-ethylpentylthio, octylthio, 2-methylheptylthio, 6-methylheptylthio, 2-ethylhexylthio, 2-ethyl-3-methylpentylthio, 3-ethyl-2-methylpentylthio, nonylthio, 2-methyloctylthio, 7-methyloctylthio, 4-ethylheptylthio, 3-ethyl-2-methylhexylthio, 2-ethyl-1-methylhexylthio, decylthio, 1-pentylhexylthio, dodecylthio, octadecylthio, 16-methylheptadecylthio, nonadecylthio, 18-methylnonadecylthio and 3-ethyloctadecylthio groups; and groups of formula $—NR^1R^2$, $—CONR^1R^2$ and $—OCONR^1R^2$, where $R^1$ and $R^2$ are the same or different and each represents: a hydrogen atom; or an alkyl group having from 1 to 4 carbon atoms, such as methyl, ethyl, propyl, isopropyl, butyl, isobutyl, sec-butyl and t-butyl groups.

Examples of the groups and atoms which may be included in substituents (b) are: alkyl groups having from 1 to 8 carbon atoms, such as the methyl, ethyl, propyl, isopropyl, butyl, isobutyl, sec-butyl, t-butyl, pentyl, 3-methylbutyl, 2,2-dimethylpropyl, 1,1-dimethylpropyl, hexyl, 1-methylpentyl, 4-methylpentyl, heptyl, 1-methylhexyl, 2-methylhexyl, 5-methylhexyl, 3-ethylpentyl, octyl, 2-methylheptyl, 6-methylheptyl, 2-ethylhexyl, 2-ethyl-3-methylpentyl and 3-ethyl-2-methylpentyl groups; and hydroxy, alkoxy, aryl, aryloxy, aliphatic acyloxy, aromatic acyloxy, carboxy, alkoxycarbonyl, aryloxycarbonyl, mercapto, alkylthio, arylthio, aralkylthio, aralkyldithio, aryldithio, alkyldithio, alkylsulphinyl, arylsulphinyl, alkylsulphonyl, arylsulphonyl, cyano, aliphatic and aromatic acyl and heterocyclic groups and groups of formula $—NR^1R^2$, $—CONR^1R^2$ and $—OCONR^1R^2$, wherein $R^1$ and $R^2$ are as defined above, and halogen atoms, as exemplified in relation to substituents (a).

Substituent (c) may be an oxygen atom as part of an oxo group ($>C=O$) with the carbon atom to which it is attached, or it may be various other groups and atoms as exemplified above in relation to substituents (a) and (b).

Preferred classes of compounds of the present invention include those compounds of formula (I) in which $R_1$, $R_2$, $R_3$, $R_4$, $R_5$, and $R_6$ are independently hydrogen, alkyl, alkoxy, aryl and at least two of them form cycloalkyl or cycloalkenyl groups having 3 to 8 members substituted with alkyl, alkenyl, or alkynyl groups having from 6 to 22 carbon atoms or substituted by at least one of substituent such as hydroxy groups, protected hydroxy groups, amino groups, protected amino groups.

$R_1$ and $R_6$ are preferably selected from alkyl, cycloalkyl, cycloalkenyl or $—CONR^1R^2$, where $R^1$ and $R^2$ are the same or different and each represents an alkyl group having from 1 to 4 carbon atoms, an alkylcarbonyl group having a total of from 2 to 5 carbon atoms, a benzoyl group, a substituted benzoyl group in which the substituents are selected from substituents (b), defined above; phenyl groups, substituted phenyl groups in which the substituents are selected from substituents (b), defined above, heterocyclic groups having 5 or 6 ring atoms, of which 1 is a nitrogen and/or oxygen and/or sulphur hetero-atom, and halogen atoms.

X, Y is selected from O, NR' or S, and more preferably both of X and Y are O.

More preferred classes of compounds of the present invention include those compounds of formula (I) wherein $R_2$, $R_4$ form a single bond, $R_3$, $R_5$ are hydrogen or substituted or unsubstituted alkyl having from 1 to 20 carbon atoms, or substituted or unsubstituted alkenyl group 1 to 20 carbon atoms, $R_1$ is a substituted alkyl or alkenyl group, or aryl group having from 1 to 20 carbon atoms. $R_1$ is preferably selected from an aryl group, which is substituted by at least one of substituents selected from substituents (b), such as hydroxy groups, protected hydroxy groups, amino groups, protected amino groups, carboxy groups, protected carboxy groups, mercapto groups, protected mercapto groups, alkoxy groups having from 1 to 8 carbon atoms and alkylthio groups having 1 or 2 carbon atoms.

$R_6$ is selected from substituents (a), and is preferably $NR^1R^2$, wherein $NR^1R^2$ represents a substituted or unsubstituted aryl, substituted or unsubstituted pyridyl, substituted or unsubstituted pyridonyl, substituted or unsubstituted pyrrolidonyl, substituted or unsubstituted uracilyl, substituted or unsubstituted piperidyl, substituted or unsubstituted piperidino, substituted or unsubstituted pyrrolidinyl, substituted or unsubstituted morpholino, substituted or unsubstituted morpholinyl, substituted or unsubstituted piperazinyl, substituted or unsubstituted thiomorpholino, substituted or unsubstituted dioxolanyl, cyclic imido (a group formed by removing hydrogen bound to an imido N atom). The examples of $R^1$ and $R^2$ include furanyl, benzofuranyl, chromenyl, pyridyl, pyrrolyl, indolyl, quinolinyl, N-alkyl pyrrolyl, 25 pyridyl-N-oxide, pyrimidoyl, pyrazinyl, imidazolyl, pyrazolyl, oxazolyl, benzothiophenyl, purinyl, indolizinyl, thienyl and the like.

X, and Y represent O, NR' or S, and preferably O.

In any of the compounds of the present invention which contains a hydroxy, amino, mercapto or carboxy group, any of these groups may be protected by a suitable protecting group. Where the protecting group is on a compound intended for use merely as a chemical intermediate, its nature is not critical to the invention; and any of the well known protecting groups may be employed. Where the resulting compound is intended for therapeutic use, the protecting group should be pharmaceutically acceptable.

Examples of hydroxy-protecting groups include: formyl, acetyl, propionyl, butyryl, isobutyryl, pentanoyl, pivaloyl, valeryl, isovaleryl, chloroacetyl, dichloroacetyl, trichloroacetyl, trifluoroacetyl. benzoyl, 4-nitrobenzoyl, 2-nitrobenzoyl, tetrahydropyran-2-yl, 3-bromotetrahydropyran-2-yl, 4-methoxytetrahydropyran-4-yl, tetrahydrothiopyran-2-yl and 4-methoxytetrahydrothiopyran-4-yl, trimethylsilyl, triethylsilyl, isopropyldimethylsilyl, t-butyldimethylsilyl, methyldiisopropylsilyl, methyldi-t-butylsilyl, triisopropylsilyl, diphenylmethylsilyl, diphenylbutylsilyl, diphenylisopropylsilyl, phenyldiisopropylsilyl, methoxymethyl, 1-ethoxyethyl, 1-(isopropoxy)ethyl, 2,2,2-trichloroethyl, benzyl, α-naphthylmethyl, β-naphthylmethyl, diphenylmethyl, triphenylmethyl, α-naphthyldiphenylmethyl and 9-anthrylmethyl, 4-methylbenzyl, 4,4'-dimethoxytriphenylmethyl, 2-nitrobenzyl, 4-nitrobenzyl, 4-chlorobenzyl, 4-bromobenzyl, 4-cyanobenzyl, 4-cyanobenzyldiphenylmethyl.

The compounds of the invention may contain asymmetric carbon atoms and/or carbon-carbon double bonds and can, therefore, form optical and/or cis/trans isomers. Although these are all referred to herein by a single formula, the present invention envisages both mixtures of the isomers as well as the individual isolated isomers.

Many of the compounds of the present invention have the anti-tumor activity referred to above. Others may be of value as intermediates in the preparation of other compounds of the present invention, which may have a greater activity.

Examples of specific compounds of the present invention are those compounds of formula (II) (Table 1) and formula (III) (Table 2).

TABLE 1

(II)

| Cpd No. | $R_1$ | $R_2$ | $R_3$ | $R_4$ | $R_5$ | $R_6$ |
|---|---|---|---|---|---|---|
| 1 | —CH═CHCH₂CH₂— | H | H | | | —CH₂CH₂CH═CH— |
| 2 | —C(CH₃)═CHCH₂CH₂— | H | H | | | —CH₂—CH₂CH═C(CH₃)— |
| 3 | —C(CH₃)═CHCH₂CH(C(CH₃)═CH₂)— | H | H | | | —CH(C(CH₃)═CH₂)CH₂CH═C(CH₃)— |
| 4 | —CBr(CH₃)CH(Br)CH₂CH(C(CH₃)═CH₂)— | H | H | | | —CH(C(CH₃)═CH₂)CH₂CH(Br)CBr(CH₃)— |
| 5 | —CBr(CH₃)CH(Br)CH₂CH(C(CH₃)═CH₂)— | H | H | | | —CH(C(CH₃)═CH₂)CH₂CH═C(CH₃)— |
| 6 | —C(CH₃)═CBrCH₂CH(C(CH₃)═CH₂)— | H | H | | | —CH(C(CH₃)═CH₂)CH₂CBr═C(CH₃)— |
| 7 | —CH(CH₃)CH₂CH₂CH(C(CH₃)═CH₂)— | H | H | | | —CH(C(CH₃)═CH₂)CH₂CH═C(CH₃)— |
| 8 | —CH(CH₃)CH₂CH₂CH(C(CH₃)═CH₂)— | H | H | | | —CH(C(CH₃)═CH₂)CH₂CH₂CH(CH₃)— |
| 9 | —CH═C(CH₃)CH₂C((CH₃)₂)— | H | H | | | —C((CH₃)₂)CH₂C(CH₃)═CH— |
| 10 | —CH═C(N(CH₃)₂)CH₂C((CH₃)₂)— | H | H | | | —C((CH₃)₂)CH₂C(N(CH₃)₂)═CH— |
| 11 | —CH(Br)CH(Br)CH₂CH₂— | H | H | | | —CH₂CH₂CH(Br)CH(Br)— |
| 12 | —CH═CHC((CH₃)₂)CH₂— | H | H | | | —CH₂C((CH₃)₂)CH═CH— |
| 13 | —CH₂CH₂CH₂CH₂— | H | H | | | —CH₂CH₂CH₂CH₂— |
| 14 | —CH₂CH₂CH(Ph)CH₂— | H | H | | | —CH₂CH(Ph)CH₂CH₂— |
| 15 | —CH═C(OCH₂CH₃)CH₂CH₂— | H | H | | | —CH₂CH₂C(OCH₂CH₃)═CH— |
| 16 | (= $R_1$, = R2 structure: 4-methoxyphenethyl) | | H | H | | (= $R_6$, = $R_5$ structure: 4-methoxyphenethyl) |
| 17 | (= $R_1$, = R2 structure: phenethyl) | | H | H | | (= $R_6$, = $R_5$ structure: phenethyl) |
| 18 | (= $R_1$, = R2 structure: 2-(phenoxymethyl)) | | H | H | | (= $R_6$, = $R_5$ structure: 2-(phenoxymethyl)) |

TABLE 1-continued (II)

$$R_1 \underset{\underset{R_2}{|}}{\overset{\overset{O}{\|}}{C}} - \underset{\underset{H}{|}}{\overset{\overset{R_3}{|}}{C}} - \underset{\underset{H}{|}}{\overset{\overset{R_4}{|}}{C}} - \underset{\underset{O}{\|}}{\overset{\overset{R_5}{|}}{C}} - R_6$$

| Cpd No. | $R_1$ | $R_2$ | $R_3$ | $R_4$ | $R_5$ | $R_6$ |
|---|---|---|---|---|---|---|
| 19 | —CH(epoxy)CHCH$_2$CH$_2$— | | H | H | | —CH$_2$—CH$_2$CH(epoxy)— |
| 20 | —CH(OH)CH(F)CH$_2$CH$_2$— | | H | H | | —CH$_2$CH$_2$CH(F)CH(OH)— |
| 21 | —CH(OCH$_3$)CH(F)CH$_2$CH$_2$— | | H | H | | —CH$_2$CH$_2$CH(F)CH(OCH$_3$)— |
| 22 | Ph-CH(CH$_3$)-O- (=R$_1$, =R$_2$) | | H | H | | Ph-CH(CH$_3$)-O- (=R$_5$, =R$_6$) |
| 23 | —CH=CHCH$_3$ | CH$_3$ | H | H | CH$_3$ | —CH=CHCH$_3$ |
| 24 | CH$_3$ | H | H | H | H | CH$_3$ |
| 25 | CH$_3$ | | (benzene) | | | CH$_3$ |
| 26 | Ph— | CH$_3$ | H | H | CH$_3$ | Ph— |
| 27 | (1-methylcyclohexenyl) | H | H | H | H | (1-methylcyclohexenyl) |
| 28 | —CH=C(CH$_3$)$_2$ | H | H | H | H | —CH=C(CH$_3$)$_2$ |
| 29 | —CH=C(CH$_3$)$_2$ | H | H | H | —CH$_2$COCH=C(CH$_3$)$_2$ | —CH=C(CH$_3$)$_2$ |
| 30 | —CH=CH(CH$_2$)$_3$CH$_3$ | H | H | H | H | —CH=CH(CH$_2$)$_3$CH$_3$ |
| 31 | PhCH=CHCH$_3$— | H | H | H | H | PhCH=CHCH$_3$— |
| 32 | 3-Cl-C$_6$H$_4$-CH=CH- | H | H | H | H | 3-Cl-C$_6$H$_4$-CH=CH- |
| 33 | 3,4-(CH$_3$O)$_2$-C$_6$H$_3$-CH=CH- | H | H | H | H | 3,4-(CH$_3$O)$_2$-C$_6$H$_3$-CH=CH- |
| 34 | 3,4-methylenedioxy-C$_6$H$_3$-CH=CH- | H | H | H | H | 3,4-methylenedioxy-C$_6$H$_3$-CH=CH- |

TABLE 1-continued (II)

Structure: R₁-C(=O)-CR₂R₃-CR₄R₅-C(=O)-R₆

| Cpd No. | R₁ | R₂ | R₃ | R₄ | R₅ | R₆ |
|---|---|---|---|---|---|---|
| 35 | 4-HO-C₆H₄-CH=CH-CH₃ | H | H | H | H | 4-HO-C₆H₄-CH=CH-CH₃ |
| 36 | 4-F₃C-C₆H₄-CH=CH-CH₃ | H | H | H | H | 4-F₃C-C₆H₄-CH=CH-CH₃ |
| 37 | —CH=CHCH₂CH₂— | | H | H | H | —CH=C(CH₃)₂ |
| 38 | —CH=CHCH₂CH₂— | | H | H | CH₃ | —CH=CHCH₃ |
| 39 | C₆H₅-CH=CH-CH₃ | H | H | H | CH₃ | —CH=CHCH₃ |
| 40 | C₆H₅-CH=CH-CH₃ | H | H | H | —CH₂CH₂CH=CH— | |
| 41 | 2-CH₃O-C₆H₄-CH=CH-CH₃ | H | H | H | —CH₂CH₂CH=CH— | |
| 42 | 2-CH₃-C₆H₄-CH=CH-CH₃ | H | H | H | —CH₂CH₂CH=CH— | |
| 43 | 2-Cl-C₆H₄-CH=CH-CH₃ | H | H | H | —CH₂CH₂CH=CH— | |
| 44 | 2-F-C₆H₄-CH=CH-CH₃ | H | H | H | —CH₂CH₂CH=CH— | |
| 45 | 2-CF₃-C₆H₄-CH=CH-CH₃ | H | H | H | —CH₂CH₂CH=CH— | |
| 46 | 3-CH₃O-C₆H₄-CH=CH-CH₃ | H | H | H | —CH₂CH₂CH=CH— | |

TABLE 1-continued $$\underset{R_2}{\overset{O}{\underset{\|}{R_1}}}\overset{R_3}{\underset{|}{C}}\overset{R_4}{\underset{|}{C}}\overset{R_5}{\underset{\|}{C}}R_6 \tag{II}$$

| Cpd No. | R₁ | R₂ | R₃ | R₄ | R₅ | R₆ |
|---|---|---|---|---|---|---|
| 47 | 3-methyl-styryl | H | H | H | —CH₂CH₂CH=CH— | |
| 48 | 3-chloro-styryl | H | H | H | —CH₂CH₂CH=CH— | |
| 49 | 3-trifluoromethyl-styryl | H | H | H | —CH₂CH₂CH=CH— | |
| 50 | 4-methoxy-styryl | H | H | H | —CH₂CH₂CH=CH— | |
| 51 | 4-methyl-styryl | H | H | H | —CH₂CH₂CH=CH— | |
| 52 | 4-chloro-styryl | H | H | H | —CH₂CH₂CH=CH— | |
| 53 | 4-hydroxy-styryl | H | H | H | —CH₂CH₂CH=CH— | |
| 54 | 4-trifluoromethyl-styryl | H | H | H | —CH₂CH₂CH=CH— | |
| 55 | 4-(dimethylamino)-styryl | H | H | H | —CH₂CH₂CH=CH— | |
| 56 | 4-phenoxy-styryl | H | H | H | —CH₂CH₂CH=CH— | |

TABLE 1-continued
(II)
| Cpd No. | R₁ | R₂ | R₃ | R₄ | R₅ | R₆ |
|---|---|---|---|---|---|---|
| 57 | 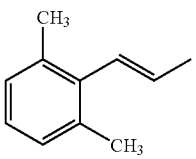 | H | H | H | | —CH₂CH₂CH=CH— |
| 58 | 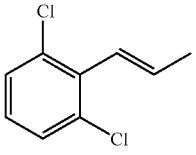 | H | H | H | | —CH₂CH₂CH=CH— |
| 59 | 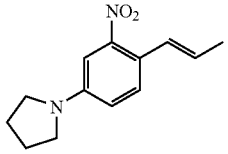 | H | H | H | | —CH₂CH₂CH=CH— |
| 60 | 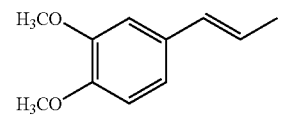 | H | H | H | | —CH₂CH₂CH=CH— |
| 61 | 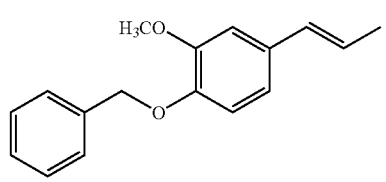 | H | H | H | | —CH₂CH₂CH=CH— |
| 62 | 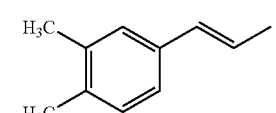 | H | H | H | | —CH₂CH₂CH=CH— |
| 63 | 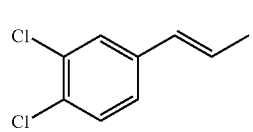 | H | H | H | | —CH₂CH₂CH=CH— |
| 64 | 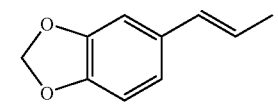 | H | H | H | | —CH₂CH₂CH=CH— |
| 65 | 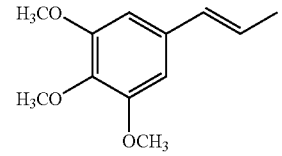 | H | H | H | | —CH₂CH₂CH=CH— |

TABLE 1-continued (II)

$$R_1-\underset{\underset{R_2}{|}}{\overset{\overset{O}{\|}}{C}}-\underset{\underset{R_3}{|}}{\overset{\overset{R_4}{|}}{C}}-\underset{\underset{O}{\|}}{\overset{R_5}{C}}-R_6$$

| Cpd No. | R₁ | R₂ | R₃ | R₄ | R₅ | R₆ |
|---|---|---|---|---|---|---|
| 66 | 2-pyridyl-CH₂– | H | H | H | —CH₂CH₂CH=CH— | |
| 67 | 3-pyridyl-CH₂– | H | H | H | —CH₂CH₂CH=CH— | |
| 68 | 4-pyridyl-CH₂– | H | H | H | —CH₂CH₂CH=CH— | |

TABLE 2

(III)

$$R_1-\underset{\underset{R_2}{|}}{\overset{\overset{X}{\|}}{C}}=\underset{}{\overset{R_4}{C}}-\underset{\underset{O}{\|}}{C}-R_6$$

| Cpd No. | R₁ | R₂ | X | R₄ | R₆ |
|---|---|---|---|---|---|
| 69 | phenyl | H | O | H | phenyl |
| 70 | phenyl | H | O | H | —OCH₃ |
| 71 | 4-fluoro-N-methylanilino | H | O | H | —OCH₃ |
| 72 | styryl | H | O | H | —OH |
| 73 | 3,4-dimethoxystyryl | H | O | H | —OH |

TABLE 2-continued (III)

| Cpd No. | R₁ | R₂ | X | R₄ | R₆ |
|---|---|---|---|---|---|
| 74 | 3,4,5-trimethoxyphenyl-CH=CH-CH₃ | H | O | H | —OH |
| 75 | phenyl-CH=CH-CH₃ | H | O | H | —OCH₂CH₃ |
| 76 | 3,4-dimethoxyphenyl-CH=CH-CH₃ | H | O | H | —OCH₂CH₃ |
| 77 | 3,4-dimethoxyphenyl-CH=CH-CH₃ | H | O | H | —OCH₂CH₃ |
| 78 | 3,4,5-trimethoxyphenyl-CH=CH-CH₃ | H | O | H | —OCH₂CH₃ |
| 79 | phenyl-CH=CH-CH₃ | H | O | H | —N(CH₃)CH₂CH₂CH₃ |
| 80 | 2-methoxyphenyl-CH=CH-CH₃ | H | O | H | —N(CH₃)CH₂CH₂CH₃ |
| 81 | 2-methylphenyl-CH=CH-CH₃ | H | O | H | —N(CH₃)CH₂CH₂CH₃ |
| 82 | 2-chlorophenyl-CH=CH-CH₃ | H | O | H | —N(CH₃)CH₂CH₂CH₃ |
| 83 | 3-chlorophenyl-CH=CH-CH₃ | H | O | H | —N(CH₃)CH₂CH₂CH₃ |

TABLE 2-continued (III)

| Cpd No. | R₁ | R₂ | X | R₄ | R₆ |
|---|---|---|---|---|---|
| 84 | 4-methoxy styryl (H₃CO-C₆H₄-CH=CH-) | H | O | H | —N(CH₃)CH₂CH₂CH₃ |
| 85 | 4-hydroxy styryl (HO-C₆H₄-CH=CH-) | H | O | H | —N(CH₃)CH₂CH₂CH₃ |
| 86 | 2,6-dimethoxy styryl | H | O | H | —N(CH₃)CH₂CH₂CH₃ |
| 87 | 2,6-dichloro styryl | H | O | H | —N(CH₃)CH₂CH₂CH₃ |
| 88 | 3,4-dimethoxy styryl | H | O | H | —N(CH₃)CH₂CH₂CH₃ |
| 89 | 4-benzyloxy-3-methoxy styryl | H | O | H | —N(CH₃)CH₂CH₂CH₃ |
| 90 | 3,4-dichloro styryl | H | O | H | —N(CH₃)CH₂CH₂CH₃ |
| 91 | 3,4,5-trimethoxy styryl | H | O | H | —N(CH₃)CH₂CH₂CH₃ |
| 92 | 4-pyridyl | H | O | H | —N(CH₃)CH₂CH₂CH₃ |

TABLE 2-continued (III)

| Cpd No. | R₁ | R₂ | X | R₄ | R₆ |
|---|---|---|---|---|---|
| 93 | (E)-styryl | H | O | H | —NHPh |
| 94 | (E)-4-methoxystyryl | H | O | H | —NHPh |
| 95 | (E)-4-chlorostyryl | H | O | H | —NHPh |
| 96 | (E)-2,6-dimethylstyryl | H | O | H | —NHPh |
| 97 | (E)-2,6-dichlorostyryl | H | O | H | —NHPh |
| 98 | (E)-3,4-dimethoxystyryl | H | O | H | —NHPh |
| 99 | (E)-3,4,5-trimethoxystyryl | H | O | H | —NHPh |
| 100 | (E)-2-(pyridin-4-yl)vinyl | H | O | H | —NHPh |
| 101 | 4-methylpyridin-3-yl | H | O | H | —NHPh |
| 102 | (E)-styryl | H | O | H | 4-methylpiperazin-1-yl |

TABLE 2-continued
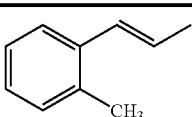
(III)
| Cpd No. | R₁ | R₂ | X | R₄ | R₆ |
|---|---|---|---|---|---|
| 103 | 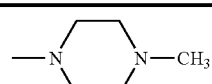 | H | O | H | 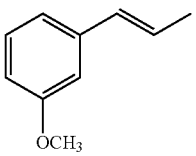 |
| 318 | 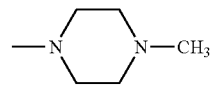 | H | O | H | 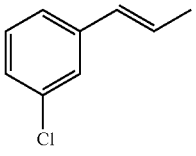 |
| 104 | 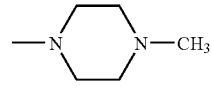 | H | O | H | 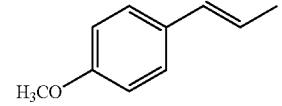 |
| 105 | 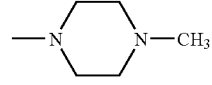 | H | O | H | 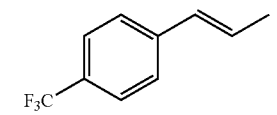 |
| 106 | 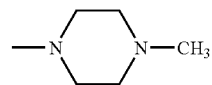 | H | O | H | 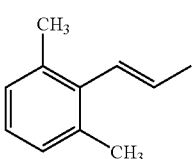 |
| 107 | 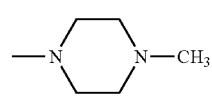 | H | O | H | 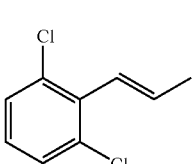 |
| 108 | 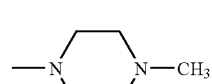 | H | O | H | 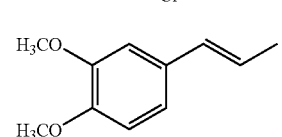 |
| 109 | 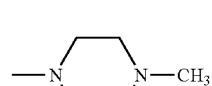 | H | O | H | 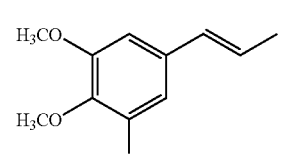 |
| 110 | 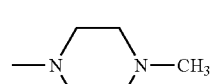 | H | O | H | |

TABLE 2-continued (III)

| Cpd No. | R₁ | R₂ | X | R₄ | R₆ |
|---|---|---|---|---|---|
| 111 | (E)-2-(pyridin-4-yl)ethenyl | H | O | H | 4-methylpiperazin-1-yl |
| 112 | 4-methylpyridin-... (pyridin-4-ylmethyl) | H | O | H | 4-methylpiperazin-1-yl |
| 113 | (E)-2-phenylethenyl | H | O | H | 4-(pyridin-4-yl)piperazin-1-yl |
| 114 | (E)-2-(2-methylphenyl)ethenyl | H | O | H | 4-(pyridin-4-yl)piperazin-1-yl |
| 115 | (E)-2-(4-methoxyphenyl)ethenyl | H | O | H | 4-(pyridin-4-yl)piperazin-1-yl |
| 116 | (E)-2-(4-trifluoromethylphenyl)ethenyl | H | O | H | 4-(pyridin-4-yl)piperazin-1-yl |
| 117 | (E)-2-(2,6-dimethylphenyl)ethenyl | H | O | H | 4-(pyridin-4-yl)piperazin-1-yl |
| 118 | (E)-2-(2,6-dichlorophenyl)ethenyl | H | O | H | 4-(pyridin-4-yl)piperazin-1-yl |
| 119 | (E)-2-(3,4-dimethoxyphenyl)ethenyl | H | O | H | 4-(pyridin-4-yl)piperazin-1-yl |
| 120 | (E)-2-(3,4,5-trimethoxyphenyl)ethenyl | H | O | H | 4-(pyridin-4-yl)piperazin-1-yl |

TABLE 2-continued (III)

| Cpd No. | R₁ | R₂ | X | R₄ | R₆ |
|---|---|---|---|---|---|
| 121 | 4-pyridyl-CH=CH-CH₃ | H | O | H | -N(piperazine)N-(4-pyridyl) |
| 122 | 4-methylpyridine | H | O | H | -N(piperazine)N-(4-pyridyl) |
| 123 | phenyl-CH=CH-CH₃ | H | O | H | -N(piperazine)N-phenyl |
| 124 | 2,6-dimethylphenyl-CH=CH-CH₃ | H | O | H | -N(piperazine)N-phenyl |
| 125 | 3,4-dimethoxyphenyl-CH=CH-CH₃ | H | O | H | -N(piperazine)N-phenyl |
| 126 | 3,4,5-trimethoxyphenyl-CH=CH-CH₃ | H | O | H | -N(piperazine)N-phenyl |
| 127 | phenyl-CH=CH-CH₃ | H | O | H | N-pyrrolidinyl |
| 128 | 2-methylphenyl-CH=CH-CH₃ | H | O | H | N-pyrrolidinyl |
| 129 | 3-methoxyphenyl-CH=CH-CH₃ | H | O | H | N-pyrrolidinyl |
| 130 | 4-trifluoromethylphenyl-CH=CH-CH₃ | H | O | H | N-pyrrolidinyl |

TABLE 2-continued (III)

| Cpd No. | R₁ | R₂ | X | R₄ | R₆ |
|---|---|---|---|---|---|
| 131 | 2,6-dimethylphenyl-CH=CH-CH₃ | H | O | H | 1-pyrrolidinyl (N-methyl) |
| 132 | 3,4-dimethoxyphenyl-CH=CH-CH₃ | H | O | H | 1-pyrrolidinyl (N-methyl) |
| 133 | phenyl-CH=CH-CH₃ | H | NOCH₃ | H | —OH |
| 134 | phenyl-CH=CH-CH₃ | H | NOCH₃ | H | —N(CH₃)CH₂CH₂CH₃ |
| 135 | 3,4,5-trimethoxyphenyl-CH=CH-CH₃ | H | NOCH₃ | H | 4-methylpiperazin-1-yl (N-methyl) |
| 136 | 3,4-dimethoxyphenyl-CH=CH-CH₃ | H | NOH | H | 4-methylpiperazin-1-yl (N-methyl) |
| 137 | 3,4-dimethoxyphenyl-CH=CH-CH₃ | H | NOCH₃ | H | 4-methylpiperazin-1-yl (N-methyl) |
| 138 | 3,4-dimethoxyphenyl-CH=CH-CH₃ | H | N—O—phenyl | H | 4-methylpiperazin-1-yl (N-methyl) |
| 139 | 3,4-dimethoxyphenyl-CH=CH-CH₃ | H | N—O—CH₂—phenyl | H | 4-methylpiperazin-1-yl (N-methyl) |

TABLE 2-continued (III)

$$\underset{R_1}{\overset{X}{\underset{\|}{C}}}\underset{R_2}{\overset{R_4}{C}}=\underset{\underset{O}{\|}}{C}\underset{R_6}{}$$

| Cpd No. | R₁ | R₂ | X | R₄ | R₆ |
|---|---|---|---|---|---|
| 140 | 3,4-dimethoxystyryl | H | benzyloxyimino (=N-O-CH₂-C₆H₅) | H | 4-(pyridin-4-yl)piperazin-1-yl |
| 141 | 3,4-dimethoxystyryl | H | benzyloxyimino (=N-O-CH₂-C₆H₅) | H | pyrrolidin-1-yl |
| 142 | 3,4-dimethoxystyryl | H | =N—O—CH₂—C(O)—N(pyrrolidin-1-yl) | H | 4-(pyridin-4-yl)piperazin-1-yl |
| 143 | 3,4-dimethoxystyryl | H | =N—O—CH₂CH₂—N(CH₃)₂ | H | 4-(pyridin-4-yl)piperazin-1-yl |
| 144 | styryl | H | N—O— | | —OH |
| 145 | styryl | H | N—O— | | —N(CH₃)CH₂CH₂CH₃ |
| 146 | styryl | H | N—O— | | —OCH₂CH₃ |

The preparation of compounds of Formula (II) in this invention is illustrated in Scheme 1. The syntheses of the diketones using the oxidative coupling of lithium enolates was described by Ito et al (Ito et al. *J. Ame. Chem. Soc*, 1977, 1487) and Frazier et al (*J. Org. Chem.*, 1980, 45, 5408). LDA was prepared by adding n-butyllithium to a solution of diisopropylamine in anhydrous solvent at 0° C. and stirred for 30-60 min at 0° C. The monoketone or the combination of two different ketones (for cross coupling) was added dropwise to the LDA solution at −78° C. After the mixture was stirred for 60 min at this temperature, anhydrous copper chloride or ferric chloride solution in solvent was added dropwise to the cold reaction solution. The resulting black mixture was allowed to warm to room temperature and stirred for overnight. 1 N HCl was added and the mixture was extracted with organic solvents. The combined organic layers were washed with water, brine, dried and concentrated to give a residue. The crude product was purified on a silica gel column or crystallized from appropriate solvents to give the desired product.

Scheme 1

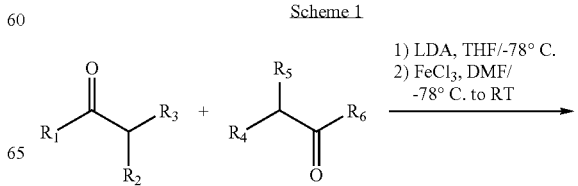

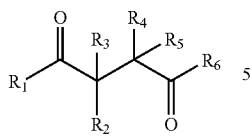

The compounds of the present invention may be prepared by a variety of methods well known in the prior art for preparing diketone compounds from the corresponding monoketone or the combination of different ketones.

The reaction is preferably conducted in the presence of an inert solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene; halogenated hydrocarbons, especially aromatic and aliphatic hydrocarbons, such as methylene chloride, chloroform, carbon tetrachloride, dichloroethane, chlorobenzene and the dichlorobenzenes; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; ketones, such as acetone, methyl ethyl ketone, methyl isobutyl ketone, isophorone and cyclohexanone; nitro compounds, which may be nitroalkanes or nitroaranes, such as nitroethane and nitrobenzene; nitriles, such as acetonitrile and isobutyronitrile; amides, which may be fatty acid amides, such as formamide, dimethylformamide, dimethylacetamide and hexamethylphosphoric triamide; and sulphoxides, such as dimethyl sulphoxide and sulpholane.

The reaction can take place over a wide range of temperatures, and the precise reaction temperature is not critical to the invention. In general, we find it convenient to carry out the reaction at a temperature of from −78° C. to 50° C.

The compounds of Formula (IV) in this invention can be prepared by known procedure in the prior art (e.g., U.S. Pat. No. 5,618,829 and other patents identified above).

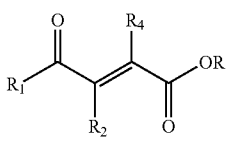

(IV)

wherein $R_1$, $R_2$, and $R_4$ are defined as in formula (I).

For example, as illustrated in Scheme 2, a solution of ketone and glyoxylic acid monohydrate in acetic acid was heated under reflux over night. Ethyl acetate was added and the mixture was washed by water, dried ($Na_2SO_4$) and concentrated. The crude product was purified by column chromatography or crystallization to provide the desired acid in moderate to good yield. The ester can be made by a variety of ester formation methods. For example, to a solution of the above made acid in dichloromethane was added a alcohol, N-(3-dimethylaminopropyl)-N'ethylcarbodiimide hydrochloride and DMAP (cat.) and the reaction was stirred at room temperature overnight. The mixture was washed by dilute HCl (~0.02N), water, dried ($Na_2SO_4$) and concentrated. The crude product was purified by column chromatography on silica gel to give the desired product.

Scheme 2

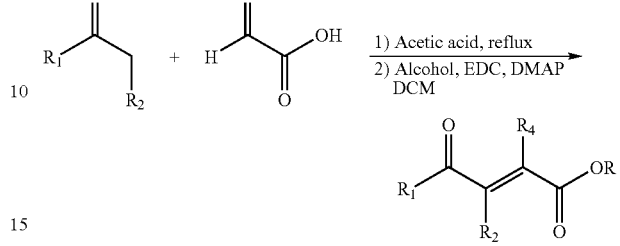

The reaction is preferably conducted in the presence of an inert solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene; halogenated hydrocarbons, especially aromatic and aliphatic hydrocarbons, such as methylene chloride, chloroform, carbon tetrachlioride, dichloroethane, chlorobenzene and the dichlorobenzenes; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; ketones, such as acetone, methyl ethyl ketone, methyl isobutyl ketone, isophorone and cyclohexanone; nitro compounds, which may be nitroalkanes or nitroaranes, such as nitroethane and nitrobenzene; nitriles, such as acetonitrile and isobutyronitrile; amides, which may be fatty acid amides, such as formamide, dimethylformamide, dimethylacetamide and hexamethylphosphoric triamide; and sulphoxides, such as dimethyl sulphoxide and sulpholane.

The reaction can take place over a wide range of temperatures, and the precise reaction temperature is not critical to the invention. In general, we find it convenient to carry out the reaction at a temperature of from −50° C. to 100° C.

The compound of formula (V) in this invention can be carried out by methods known in the art (e.g., U.S. Pat. No. 5,618,829 and other patents identified above).

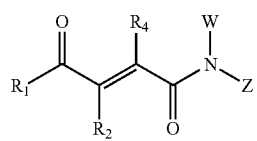

(V)

wherein $R_1$, $R_2$, and $R_4$ are defined as in formula (I).

The preparations are illustrated in Scheme 3. After the carboxylic acid was obtained from the reaction such as illustrated in Scheme 2, a amide can be made by a variety of amide formation methods. For example, to a solution of the carboxylic acid in dichloromethane was added N-methylpropylamine, HOBt, $Et_3N$ and EDC at 0° C. and the mixture was stirred at room temperature overnight. 1N HCl was added and the mixture was extracted with dichloromethane. The combined organic layer was washed by sodium bicarbonate, brine, dried (Na$_2$SO$_4$) and concentrated. The crude product was purified by column chromatography on silica gel give the desired product.

Scheme 3

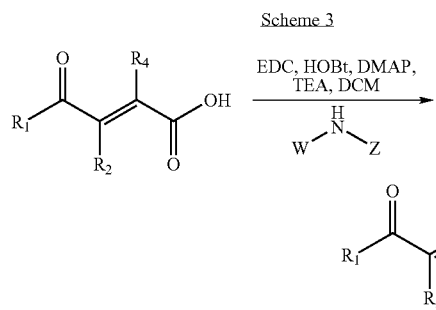

The reaction is preferably conducted in the presence of an inert solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene; halogenated hydrocarbons, especially aromatic and aliphatic hydrocarbons, such as methylene chloride, chloroform, carbon tetrachloride, dichloroethane, chlorobenzene and the dichlorobenzenes; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; ketones, such as acetone, methyl ethyl ketone, methyl isobutyl ketone, isophorone and cyclohexanone; nitro compounds, which may be nitroalkanes or nitroaranes, such as nitroethane and nitrobenzene; nitriles, such as acetonitrile and isobutyronitrile; amides, which may be fatty acid amides, such as formamide, dimethylformamide, dimethylacetamide and hexamethylphosphoric triamide; and sulphoxides, such as dimethyl sulphoxide and sulpholane.

The reaction can take place over a wide range of temperatures, and the precise reaction temperature is not critical to the invention. In general, we find it convenient to carry out the reaction at a temperature of from −50° C. to 100° C.

The compound of formula (VI) in this invention can be carried out by a procedure known in the prior art (e.g., *J. Med. Chem.*, 2003, 46, 2534, and other articles describing the preparation of oximes).

Formula (VI)

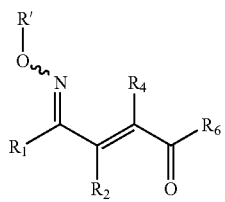

Wherein R' is a hydrogen or any other groups, and R$_1$, R$_2$, R$^4$ and R$_6$ are defined as in formula (I), preferably, R$_6$ is NR$^1$R$^2$.

The preparations are illustrated in Scheme 3. The preparation of dicarbonyl derivatives of Formula (VI) is illustrated in Scheme 4. To a solution of dicarbonyl compound in pyridine/acetic acid was added the oxyamine at room temperature and stirred at 40° C. for 2 hours. 1N HCl was added and the mixture was extracted by ethyl acetate three times. The combined organic was washed by brine, dried (Na$_2$SO$_4$) and concentrated. The crude product was purified on silica gel column to afford the desired product as isomers mixture or each isomer.

Scheme 4

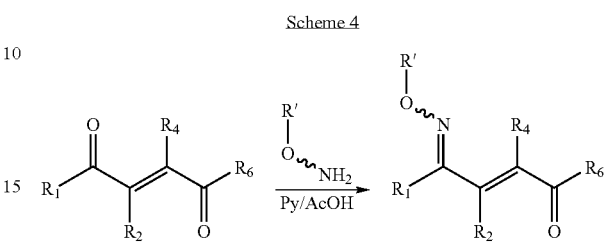

The reaction is preferably conducted in the presence of an inert solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene; halogenated hydrocarbons, especially aromatic and aliphatic hydrocarbons, such as methylene chloride, chloroform, carbon tetrachloride, dichloroethane, chlorobenzene and the dichlorobenzenes; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; ketones, such as acetone, methyl ethyl ketone, methyl isobutyl ketone, isophorone and cyclohexanone; nitro compounds, which may be nitroalkanes or nitroaranes, such as nitroethane and nitrobenzene; nitriles, such as acetonitrile and isobutyronitrile; amides, which may be fatty acid amides, such as formamide, dimethylformamide, dimethylacetamide and hexamethylphosphoric triamide; and sulphoxides, such as dimethyl sulphoxide and sulpholane.

The reaction can take place over a wide range of temperatures, and the precise reaction temperature is not critical to the invention. In general, we find it convenient to carry out the reaction at a temperature of from −50° C. to 100° C.

The compounds of formula (VII) in this invention can be prepared with the procedure in the prior art (e.g., *J. Am. Chem. Soc.*, 2005, 127, 210, and other articles describing the preparation of isoxazoles).

(VII)

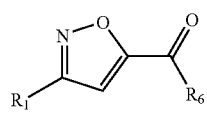

The preparation of dicarbonyl derivatives of Formula (VII) is illustrated in Scheme 5. To a solution of hydroxylamine hydrochloride in 1:1 t-BuOH:H$_2$O was added the aldehyde, followed by NaOH. After stirred until oxime formation was complete, Chloramine-T trihydrate was added, followed by CuSO$_4$.5H$_2$O and copper turnings. Substituted acetylene was added and pH was adjusted to ca. 6 by addition of a few drops of 1 M NaOH, and stirring was continued for overnight. The reaction mixture was poured into ice/water (150 mL), and 1N HCl was added to adjust the PH~2. The product was collected by filtration. Purification can be achieved by either crystallization of column chromatography.

Scheme 5

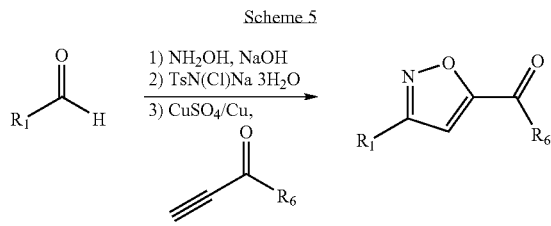

The reaction is preferably conducted in the presence of an inert solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene; halogenated hydrocarbons, especially aromatic and aliphatic hydrocarbons, such as methylene chloride, chloroform, carbon tetrachloride, dichloroethane, chlorobenzene and the dichlorobenzenes; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; ketones, such as acetone, methyl ethyl ketone, methyl isobutyl ketone, isophorone and cyclohexanone; nitro compounds, which may be nitroalkanes or nitroaranes, such as nitroethane and nitrobenzene; nitriles, such as acetonitrile and isobutyronitrile; amides, which may be fatty acid amides, such as formamide, dimethylformamide, dimethylacetamide and hexamethylphosphoric triamide; and sulphoxides, such as dimethyl sulphoxide and sulpholane.

The reaction can take place over a wide range of temperatures, and the precise reaction temperature is not critical to the invention. In general, we find it convenient to carry out the reaction at a temperature of from −50° C. to 100° C.

The compounds of the present invention may be administered as a pharmaceutical composition containing the compounds and a pharmaceutically-acceptable carrier or diluent. The active materials can also be mixed with other active materials which do not impair the desired action and/or supplement the desired action. The active materials, in accordance with the present invention, may be administered by any acceptable route including, but not limited to, orally, parenterally, intravenously, intradermally, subcutaneously, intramuscularly, by an airborne delivery system, topically, in liquid or solid form.

Oral compositions will generally include an inert diluent or an edible carrier. Such oral compositions may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like.

The oral compositions may contain additional ingredients such as: a binder such as microcrystalline cellulose, gum tragacanth or gelatin; an excipient such as starch or lactose, a disintegrating agent such as alginic acid, corn starch and the like; a lubricant such as magnesium stearate; a glidant such as colloidal silicon dioxide; and a sweetening agent such as sucrose or saccharin or flavoring agent such as peppermint, methyl salicylate, or orange flavoring. When the dosage unit form is a capsule, it may additionally contain a liquid carrier such as a fatty oil. Other dosage unit forms may contain other various materials which modify the physical form of the dosage unit, such as, for example, a coating. Thus, tablets or pills may be coated with sugar, shellac, or other enteric coating agents. A syrup may contain, in addition to the active ingredients, sucrose as a sweetening agent and certain preservatives, dyes and colorings and flavors. Materials used in preparing these various compositions should be pharmaceutically or veterinarially pure and non-toxic in the amounts used.

For the purposes of parenteral therapeutic administration, the active ingredient may be incorporated into a solution or suspension. The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The pharmaceutical forms suitable for injectable use include sterile solutions, dispersions, emulsions, and sterile powders. The final form should be stable under conditions of manufacture and storage. Furthermore, the final pharmaceutical form should be protected against contamination and should, therefore, be able to inhibit the growth of microorganisms such as bacteria or fungi. A single intravenous or intraperitoneal dose can be administered. Alternatively, a slow long-term infusion or multiple short-term daily infusions may be utilized, typically lasting from 1 to 8 days. Alternate day dosing or dosing once every several days may also be utilized.

Sterile, injectable solutions may be prepared by incorporating a compound in the required amount into one or more appropriate solvents to which other ingredients, listed above or known to those skilled in the art, may be added as required. Sterile injectable solutions may be prepared by incorporating the compound in the required amount in the appropriate solvent with various other ingredients as required. Sterilizing procedures, such as filtration, may then follow. Typically, dispersions are made by incorporating the compound into a sterile vehicle which also contains the dispersion medium and the required other ingredients as indicated above. In the case of a sterile powder, the preferred methods include vacuum drying or freeze drying to which any required ingredients are added.

Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer. In all cases, the final form, as noted, must be sterile and should also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

In accordance with the invention, there are provided compositions containing geldanamycin derivatives and methods useful for the in vivo delivery of geldanamycin derivatives in the form of nanoparticles, which are suitable for any of the aforesaid routes of administration.

In accordance with the present invention, there are provided compositions of dicarbonyl derivative and methods useful for the in vivo delivery of dicarbonyl derivatives in the form of nanoparticles, which are suitable for aforesaid any route administrations.

U.S. Pat. Nos. 5,916,596, 6,506,405 and 6,537,579 teach the preparation of nanoparticle from the biocompatible polymers, such as albumin. Thus, in accordance with the present invention, there are provided methods for the formation of nanoparticles of present invention by a solvent evaporation technique from an oil-in-water emulsion prepared under conditions of high shear forces (e.g., sonication, high pressure homogenization, or the like).

The prepared nanoparticle with this invention can be administered by any acceptable route including, but not limited to, orally, intramuscularly, transdermally, intravenously, through an inhaler or other air borne delivery systems, and the like. When preparing the composition for injection, particularly for intravenous delivery, the continuous phase preferably comprises an aqueous solution of tonicity modifiers, buffered to a pH below 7, more preferably below 6.

The prepared nanoparticles of this invention may be enclosed in a hard or soft capsule, may be compressed into tablets, or may be incorporated with beverages, food or otherwise into the diet. Capsules may be formulated by mixing the nanoparticle with a pharmaceutical diluent which is inert and inserting this mixture into a hard gelatin capsule having the appropriate size. If soft capsules are desired a slurry of the compound with an acceptable vegetable, light petroleum, or other inert oil can be encapsulated by machine into a gelatin capsule. The percentage of the final composition and the preparations may, of course, be varied and may conveniently range between 1 and 90% of the weight of the final form, e.g., a tablet. The amount in such therapeutically useful compositions is such that a suitable dosage will be obtained. Preferred compositions according to the current invention are prepared so that an oral dosage unit form contains between about 5 to about 50% by weight (% w) in dosage units weighing between 50 and 1000 mg.

The lipophilic compounds in this invention will be more easily passed through the cell membranes and distributed tissues and cross the blood brain barrier. The tissue can be tissue of the Blood and Blood Forming system: including platelets, blood vessel wall, and bone marrow; Cardiovascular system: including heart and vascular system; Digestive and excretory system: including alimentary tract, biliary tract, kidney, liver, pancreas and urinary tract; Endocrine system: including adrenal gland, kidney, ovary, pituitary gland, renal gland, salivary gland, sebaceous gland, testis, thymus gland and thyroid gland; Muscular system: including muscles that move the body. Reproductive System: including breast, ovary, penis and uterus; Respiratory system: including bronchus, lung and trachea; Skeletal system: including bones and joints; Tissue, fiber, and integumentary system: including adipose tissue, cartilage, connective tissue, cuticle, dermis, epidermis, epithelium, fascia, hair follicle, ligament, bone marrow, melanin, melanocyte, mucous membrane, skin, soft tissue, synovial capsule and tendon.

Accordingly, the dicarbonyl derivatives of the present invention can be used in warm-blooded animals, including humans, as an anti-tumor agent against these kinds of tumoral diseases. The compounds may be administered by any convenient route, for example by parenteral administration methods, such as intravenous injection, subcutaneous injection, intramuscular injection or by suppositories; or oral administration by using, for example, capsules, powders or granules.

The dosage to an adult human may vary depending on the nature of the disease, the route of administration and the administration frequency and period. However, a daily dosage of from 1 to 100 mg in a single dose or in divided doses may be given.

For example, compositions for injection can be provided in the form of ampoules, each containing a unit dose amount, or in the form of a container containing multiple doses. The composition may sometimes contain additives such as emulsifiers, stabilizers and/or dispersants, and may often be in the form of a powder, which is intended to be dissolved by the pharmacist in a suitable solvent, such as a pyrogen-free sterilized aqueous solvent, just before use.

In accordance with the present invention, the compounds of the present invention are used to treat cancers, which include but are not limited to tumors of the nasal cavity, paranasal sinuses, nasopharynx, oral cavity, oropharynx, larynx, hypopharynx, salivary glands, and paragangliomas. The compounds of the present invention are used to treat cancers of the liver and biliary tree (particularly hepatocellular carcinoma), intestinal cancers, particularly colorectal cancer, ovarian cancer, small cell and non-small cell lung cancer, breast cancer, sarcomas (including fibrosarcoma, malignant fibrous histiocytoma, embryonal rhabdomysocarcoma, leiomyosarcoma, neuro-fibrosarcoma, osteosarcoma, synovial sarcoma, liposarcoma, and alveolar soft part sarcoma), neoplasms of the central nervous systems (particularly brain cancer), lymphomas (including Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma).

The antiangiogenic treatment defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the antiangiogenic treatment defined hereinbefore may be: surgery, radiotherapy or chemotherapy. Such chemotherapy may include the following categories of therapeutic agent:

(a) other antiangiogenic agents that work by different mechanisms from those defined hereinbefore (for example linomide, inhibitors of integrin .alpha. function, angiostatin, endostatin, razoxin, thalidomide) and including vascular endothelial growth factor (VEGF) receptor tyrosine kinase inhibitors (RTKIs) (for example, those described in International Patent Application Publication Nos. WO 97/22596, WO 97/30035, WO 97/32856 and WO 98/13354);

(b) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5.alpha.-dihydroreductase (for example finasteride), anti-invasion agents (for example metalloproteinase inhibitors like marimastat and inhibitors of urokinase plasminogen activator receptor function) and inhibitors of growth factor function, (such growth factors include for example epidermal growth factor (EGF), platelet derived growth factor and hepatocyte growth factor such inhibitors include growth factor antibodies, growth factor receptor antibodies, tyrosine kinase inhibitors and serine/threonine kinase inhibitors);

(c) biological response modifiers (for example interferon);
(d) antibodies (for example edrecolomab); and
(e) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincristine and taxoids like taxol, taxotere); enzymes (for example asparaginase); thymidylate synthase inhibitors (for example raltitrexed); topoisomerase inhibitors (for example epipodophyllotoxins like etoposide and teniposide, amsacrine, topotecan, irinotecan).

In addition to their use in therapeutic medicine, the compounds of formula (I) and their pharmaceutically acceptable salts, solvates or pro-drugs are also useful as pharmacological tools in the development and standardization of in vitro and in vivo test systems for the evaluation of the effects of vascular damaging agents in laboratory animals such as cats, dogs, rabbits, monkeys, rats and mice, as part of the search for new therapeutic agents.

Other features of the present invention will become apparent in view of the following examples, which are given for illustration of the invention and are not intended to be limiting thereof.

EXAMPLE 1

This example illustrates the preparation of Compound 1. LDA was prepared by adding n-butyllithium (21.23 mL of 1.6 M solution in hexane, 34.44 mmol) to a solution of diisopropylamine (4.87 mL diisopropylamine, 34.44 mmol) in anhydrous THF (40 mL) at 0° C. and stirred for 30-60 min at 0° C. 3-(Dimethylamino)-5,5-dimethyl-2-cyclohexen-1-one (4.66 g, 27.86 mmol) was added dropwise to the LDA solution at −78° C. After the mixture was stirred for 60 min at this temperature, anhydrous ferric chloride (40 mL of 1 M solution in DMF, 40 mmol) was added dropwise to the cold reaction solution. The resulting black mixture was allowed to warm to room temperature and stirred for overnight. 1 N HCl was added and the mixture was extracted with dichloromethane. The combined organic layers were washed with water, brine, dried ($NaSO_4$) and concentrated to give a residue. The crude product was purified by column chromatography on a silica gel (eluted with EtOAc:DCM:TEA:MeOH:: 80:20:5:5), and the solvents were removed under reduced pressure to give two purple solids of two diastereomers. Diastereomer A (17%): $^1$H NMR (500 MHz, $CDCl_3$) δ 5.00 (2H, s, COC$\underline{H}$=C(N($CH_3$)$_2$)$CH_2$), 2.94 (12H, s, N($CH_3$)$_2$), 2.72 (2H, d, J=17.1 Hz, COC$\underline{H}$C($CH_3$)$_2$), 2.34, 2.01 (4H, s, d, J=17.10 Hz, =C(N($CH_3$)$_2$)C$\underline{H}_2$) 1.11, 1.02 (12H, s, s, $CH_3$); ESI-MS: calcd for (C20H32N2O2Na) 355, found 355 (MNa$^+$). Diastereomer B (17%): $^1$H NMR (500 MHz, $CDCl_3$) δ 4.84 (2H, s, COCH=C(N($CH_3$)$_2$)$CH_2$), 3.05 (2H, d, J=16.66 Hz, COC$\underline{H}$C($CH_3$)$_2$), 2.90 (12H, s, N($CH_3$)$_2$), 2.27, 1.90 (4H, s, d, J=15.24), =C(N($CH_3$)$_2$)C$\underline{H}_2$) 1.11, 1.02 (12H, s, s, $CH_3$); ESI-MS: calcd for (C20H32N2O2Na) 355, found 355 (MNa$^+$).

EXAMPLE 2

This example illustrates the preparation of Compound 2. The synthesis procedure of Compound 2 was the same as was used in the preparation of Compound 1. Instead of using column chromatography for the purification, a crystallization method was used wherein ethyl acetate and hexanes were used as solvents. The diastereomer mixture of Compound 2 was obtained as light yellow solids (73%): $^1$H NMR (500 MHz, $CDCl_3$) δ 6.60 (2H, d, J=12.00 Hz, COC$\underline{H}$=CHC($CH_3$)$_2$), 5.84 (2H, d, J=11.77 Hz, COCH=C$\underline{H}$C($CH_3$)$_2$), 3.44, 3.03 (2H, dd, for major diastereomer, J=16.70 Hz, J=4.00 Hz, d, for minor diastereomer, J=17.19 Hz, COC$\underline{H}$C($CH_3$)$_2$), 1.93, 1.74 (2H, t, for minor diastereomer J=13.35 Hz, t, for major diastereomer, J=13.12 Hz, =CHC($CH_3$)$_2$C$\underline{H}_2$), 1.64 (2H, m, =CHC($CH_3$)$_2$C$\underline{H}_2$'), 1.26, 1.20, (6H, s, for major diastereomer, s, for minor diastereomer, $CH_3$), 1.16, 1.13, (6H, s, for minor diastereomer, s, for major diastereomer, $CH_3$); ESI-MS: calcd for (C16H22O2Na) 269, found 269 (MNa$^+$).

EXAMPLE 3

This example illustrates the preparation of Compound 3. The synthesis procedure of Compound 3 was the same as was used in the preparation of Compound 1 and column chromatography was used for the purification (silica gel, elute: 0-15% ethyl acetate in hexanes). A mixture of diastereomers was obtained as white solids (41%): $^1$H NMR (500 MHz, $CDCl_3$) δ 7.48-7.17 (10H, m, Ar$\underline{H}$), 3.32-3.10 (2H, m, C$\underline{H}$Ar), 2.62-1.00 (14H, m, COC$\underline{H}_2$C$\underline{H}_2$CH(Ar)C$\underline{H}_2$C$\underline{H}$); ESI-MS: calcd for (C24H26O2Na) 369, found 369 (MNa$^+$).

EXAMPLE 4

This example illustrates the preparation of Compound 4. The synthesis procedure of Compound 4 was the same as used in the preparation of Compound 1. Instead of using column chromatography for the purification, a crystallization method was used wherein ethyl acetate and hexanes were used as solvents. The diastereomer mixture of Compound 4 was obtained as white solids (30%): $^1$H NMR (500 MHz, $CDCl_3$) δ 5.35, 5.34 (2H, s, s, COC$\underline{H}$=C(OC$H_2$$CH_3$)), 4.12-3.83 (4H, m, =C(OC$\underline{H}_2$$CH_3$)), 3.20, 2.74 (2H, m, m, COC$\underline{H}$C$H_2$C$H_2$), 2.61-2.31 (4H, m, =C(OC$H_2$$CH_3$)C$\underline{H}_2$), 1.88-1.70 (4H, m, COCHC$\underline{H}_2$C$H_2$), 1.36-1.23 (6H, m, C$\underline{H}_3$); ESI-MS: calcd for (C16H22O4Na) 301, found 301 (MNa$^+$).

EXAMPLE 5

This example illustrates the preparation of Compound 5. The synthesis procedure of Compound 5 was the same as used in the preparation of Compound 1. Instead of using column chromatography for the purification, a crystallization method was used wherein ethyl acetate and hexanes were used as solvents. The diastereomer mixture of Compound 5 was obtained as white solids (64%): $^1$H NMR (500 MHz, CDCl$_3$) δ 8.04, 8.00 (2H, d, J=8.69 Hz, for diastereomer A, d, J=8.77 Hz, for diastereomer B, ArH), 6.84-6.80 (2H, m, ArH), 6.70 (2H, s, ArH), 3.86, 3.85 (6H, s, s, CH$_3$OAr), 3.60-2.89 (6H, m, COCHCH$_2$CH$_2$), 2.18-1.90 (4H, m, COCHCH$_2$CH$_2$); ESI-MS: calcd for (C22H22O4Na) 373, found 373 (MNa$^+$).

EXAMPLE 6

This example illustrates the preparation of Compound 6. The synthesis procedure of Compound 6 was the same as used in the preparation of Compound 1. Instead of using column chromatography for the purification, a crystallization method was used wherein ethyl acetate and hexanes were used as solvents. The diastereomer mixture of Compound 6 was obtained as light yellow solids (24%): $^1$H NMR (500 MHz, CDCl$_3$) δ 8.08, 8.03 (2H, d, J=7.86 Hz, for diastereomer A, d, J=7.84 Hz, for diastereomer B, ArH), 7.48 (2H, m, ArH), 7.32 (2H, m, ArH), 7.25 (2H, m, ArH), 3.65-2.96 (6H, m, COCHCH$_2$CH$_2$), 2.21-1.96 (4H, m, COCHCH$_2$CH$_2$); ESI-MS: calcd for (C20H18O2Na) 313, found 313 (MNa$^+$).

EXAMPLE 7

This example illustrates the preparation of Compound 7. The synthesis procedure of Compound 7 was the same as was used in the preparation of Compound 1 and column chromatography was used for the purification (silica gel, elute: 0-30% ethyl acetate in hexanes). Compound 7 was obtained as clear liquid (34%): $^1$H NMR (500 MHz, CDCl$_3$) δ 6.94 (2H, m, CH$_3$CH=CHCO), 6.15 (2H, d, J=17.27 Hz, CH$_3$CH=CHCO), 3.12 (2H, m, COCH), 1.92-1.88 (6H, m, CH$_3$CH=CHCO), 1.11-0.98 (6H, m, COCHCH$_3$); ESI-MS: calcd for (C12H18O2 Na) 217, found 217 (MNa$^+$).

EXAMPLE 8

This example illustrates the preparation of Compound 8. The synthesis procedure of Compound 8 was the same as was used in the preparation of Compound 1 and column chromatography was used for the purification (silica gel, elute: 10-75% ethyl acetate in hexanes). Compound 8 was obtained as purple color solids (14%): $^1$H NMR (500 MHz, CDCl$_3$) δ 9.21 (2H, d, J=8.30 Hz, ArH), 7.37 (2H, t, J=7.55 Hz, ArH), 7.07 (2H, t, J=8.47 Hz, ArH), 6.79 (2H, d, J=7.76 Hz, ArH), 3.29 (6H, s, CH$_3$); ESI-MS: calcd for (C18H14N2O2) 290, found 291 (MH$^+$).

EXAMPLE 9

This example illustrates the preparation of Compound 9. The synthesis procedure of Compound 9 was the same as was used in the preparation of Compound 1. Instead of using column chromatography for the purification, a crystallization method was used wherein ethyl acetate and hexanes were used as solvents. The diastereomer mixture of Compound 9 was obtained as white solids (58%): $^1$H NMR (500 MHz, CDCl$_3$) δ 7.41-7.281 (OH, m, ArH), 5.72-5.41 (2H, m, PhCH(O)CH$_2$), 3.46-3.00 (2H, m, COCH), 2.81-2.00 (4H, m, CH$_2$); ESI-MS: calcd for (C20H18O4Na) 345, found 345 (MNa$^+$).

EXAMPLE 10

This example illustrates the preparation of Compound 10. The synthesis procedure of Compound 10 was the same as was used in the preparation of Compound 1 and column chromatography was used for the purification (silica gel, elute: 0-15% ethyl acetate in hexanes). Compound 10 was obtained as white solids (48%): $^1$H NMR (500 MHz, CDCl$_3$) δ 7.00 (2H, m, CH=C(CH$_2$)CO), 2.96 (4H, s, COCH$_2$), 2.26-2.20 (8H, m, CH2C(CO)=CH2CH2), 1.64-1.58 (8H, m, CH$_2$CH$_2$); ESI-MS: calcd for (C16H22O2Na) 269, found 269 (MNa$^+$).

EXAMPLE 11

This example illustrates the preparation of Compound 11. The synthesis procedure of Compound 11 was the same as was used in the preparation of Compound 1 and column chromatography was used for the purification (silica gel, elute: 0-15% ethyl acetate in hexanes). Compound 11 was obtained as light-yellow waxy solids (24%): $^1$H NMR (500 MHz, CDCl$_3$) δ 6.12 (2H, m, COCH=), 2.71 (4H, s, COCH$_2$), 2.12 (6H, d, J=0.76 Hz, CH$_3$), 1.88 (6H, d, J=0.90 Hz, CH$_3$); ESI-MS: calcd for (C12H18O2Na) 217, found 217 (MNa$^+$).

EXAMPLE 12

This example illustrates the preparation of Compound 12. The synthesis procedure of Compound 12 was the same as was used in the preparation of Compound 1 and column chromatography was used for the purification (silica gel, elute: 0-10% ethyl acetate in hexanes). Two diastereomers of Compound 12 were obtained as white waxy solids. Diastereomer A (19%): $^1$H NMR (500 MHz, CDCl$_3$) δ 8.06 (4H, d, J=8.00 Hz, ArH), 7.60 (2H, t, J=8.47 Hz, ArH), 7.50 (4H, t, J=7.88 Hz, ArH), 4.06 (2H, m, COCH(CH$_3$)), 1.14, 1.11 (6H, s, s, CH$_3$); ESI-MS: calcd for (C18H18O2Na) 289, found 289 (MNa$^+$). Diastereomer B (36%): $^1$H NMR (500 MHz, CDCl$_3$) δ 8.00 (4H, d, J=8.30 Hz, ArH), 7.55 (2H, t, J=6.88 Hz, ArH), 7.47 (4H, t, J=8.43 Hz, ArH), 3.97 (2H, m, COCH(CH$_3$)), 1.30, 1.27 (6H, s, s, CH$_3$); ESI-MS: calcd for (C18H18O2Na) 289, found 289 (MNa$^+$).

EXAMPLE 13

This example illustrates the preparation of Compound 13. The synthesis procedure of Compound 13 was similar to the preparation of Compound 1, wherein, instead of using FeCl$_3$, a solution of CuCl$_2$ in DMF was used as the oxidative reagent. After purified by column chromatography on silica gel (elute: 0-15% ethyl acetate in hexanes), Compound 13 was obtained as purple solids (28%): $^1$H NMR (500 MHz, CDCl$_3$) δ 7.63 (2H, d, J=16.27 Hz, PhCH=CH), 7.56 (4H, m, Ar—H), 7.40 (6H, m, Ar—H), 6.80 (2H, d, J=16.27 Hz, PhCH=CH), 3.11 (4H, s, CH$_2$CH$_2$); ESI-MS: calcd for (C20H18O2Na) 313, found 313 (MNa$^+$).

EXAMPLE 14

This example illustrates the preparation of Compound 14. The synthesis procedure of Compound 14 was similar to the preparation of Compound 1, wherein, instead of using FeCl$_3$, a solution of CuCl$_2$ in DMF was used as the oxidative reagent. After purified by crystallization from ethyl acetate-hexanes, Compound 14 was obtained as yellow solids (22%): $^1$H NMR (500 MHz, CDCl$_3$) δ 7.56-7.02 (10H, m, PhCH=CH Ar—

H), 6.78 (2H, d, J=16.26, PhCH=CH), 3.08 (4H, s, CH₂CH₂); ESI-MS: calcd for (C20H16C12O2Na) 381, found 381 (MNa⁺).

EXAMPLE 15

This example illustrates the preparation of Compound 15. The synthesis procedure of Compound 15 was similar to the preparation of Compound 1, wherein, instead of using FeCl₃, a solution of CuCl₂ in DMF was used as the oxidative reagent. After purified by column chromatography on silica gel (elute: 0-5% ethyl acetate in hexanes), Compound 15 was obtained as yellow liquid (39%): $^1$H NMR (500 MHz, CDCl₃) δ 6.88 (2H, dt, $J_d$=16.03 Hz, $J_t$=6.93 Hz, COCH=CHCH₂), 6.11 (2H, d, J=15.96 Hz, COCH=CHCH₂), 2.88 (4H, s, COCH₂CH₂CO), 2.22 (4H, m, COCH=CHCH₂), 1.45 (4H, m, COCH=CHCH₂CH₂), 1.33 (4H, m, COCH=CHCH₂CH₂), 0.90 (6H, t, J=7.35 Hz, CH₃); ESI-MS: calcd for (C16H26O2Na) 273, found 273 (MNa⁺).

EXAMPLE 16

This example illustrates the preparation of Compound 16. The synthesis procedure of Compound 16 was similar to the preparation of Compound 1, wherein, instead of using FeCl₃, a solution of CuCl₂ in DMF was used as the oxidative reagent. After purified by column chromatography on silica gel (elute: 0-10% ethyl acetate in hexanes), Compound 16 was obtained as yellow solids (61%): $^1$H NMR (500 MHz, CDCl₃) δ 7.49 (2H, dd, J=11.49 Hz, J=15.32 Hz, CH₃(CH₃)C=CHCH=CHCOCH₂), 6.10 (2H, d, J=15.31 Hz, CH₃(CH₃)C=CHCH=CHCOCH₂), 6.00 (2H, d, J=11.21 Hz, CH₃(CH₃)C=CHCH=CHCOCH₂), 2.92 (4H, s, CH₃(CH₃)C=CHCH=CHCOCH₂), 1.90, 1.88 (12H, s, s, CH₃); ESI-MS: calcd for (C16H22O2Na) 269, found 269 (MNa⁺).

EXAMPLE 17

This example illustrates the preparation of Compound 17. The synthesis procedure of Compound 17 was similar to the preparation of Compound 1, wherein, instead of using FeCl₃, a solution of CuCl₂ in DMF was used as the oxidative reagent. After purified by column chromatography on silica gel (elute: 0-10% ethyl acetate in hexanes), Compound 17 was obtained as yellow solids (9%): $^1$H NMR (500 MHz, CDCl₃) δ 7.58 (2H, d, J=16.18 Hz, PhCH=CH), 7.15 (2H, d, J=8.34 Hz, Ar—H), 7.09 (2H, s, Ar—H), 6.88 (2H, d, J=8.34 Hz, Ar—H), 6.67 (2H, d, J=16.04 Hz, PhCH=CH), 3.92 (12H, s, OCH₃), 3.09 (4H, s, CH₂CH₂); ESI-MS: calcd for (C24H26O6Na) 433, found 433 (MNa⁺).

EXAMPLE 18

This example illustrates the preparation of Compound 18. The synthesis procedure of Compound 18 was similar to the preparation of Compound 1, wherein, instead of using FeCl₃, a solution of CuCl₂ in DMF was used as the oxidative reagent. After purified by column chromatography on silica gel (elute: 0-10% ethyl acetate in hexanes), Compound 18 (diastereomer mixture) was obtained as white solids (11%): $^1$H NMR (500 MHz, CDCl₃) δ 7.55 (2H, m, Ar—H), 7.21 (2H, m, Ar—H), 6.97 (2H, m, Ar—H), 4.67-4.43 (4H, m, CH₂), 3.41-3.35 (2H, m, CH); ESI-MS: calcd for (C18H12F2O4) 330, found 329 ([M-H]⁻).

EXAMPLE 19

This example illustrates the preparation of Compound 19. LDA was prepared as usual such as in the prepreation of Compound 1. 2-cyclohexene-1-one (1.00 mL, 10.30 mmol) and 4-Methyl-3-penten-2-one (0.47 mL, 4.12 mmol) were added concurrently to the LDA solution at −78° C. and stirred at this temperature for 30 min. then CuCl₂ in DMF (25.83 mL of 0.67 M, 17.30 mmol) was added at −78° C. and stirred at this temperature for 45 min. and then warmed up to room temperature and stirred overnight. Work up as usual and the crude product was purified on column, using 0-10% ethyl acetate in hexane as the eluting solvents. The desired product was obtained as yellow liquid (26%): $^1$H NMR (500 MHz, CDCl₃) δ 6.94 (1H, m, CH₂CH=CHCO), 6.11 (1H, s, COCH=C(CH₃)₂), 6.02 (1H, d, J=9.94 Hz, CH₂CH=CHCO), 3.20-2.40 (3H, m, COCHCH₂CO), 2.15 (3H, s, CH₃), 2.12-1.96 (2H, m, =CHCH₂CH₂CH), 1.89 (3H, s, CH₃), 1.79-1.62 (2H, m, =CHCH₂CH₂CH); ESI-MS: calcd for (C12H16O2Na) 215, found 215 (MNa⁺).

EXAMPLE 20

This example illustrates the preparation of Compound 20. Compound 20 was prepared by using the same method as for the preparation of Compound 19 and was obtained after purified on column (silica gel, elute: 0-10% ethyl acetate in hexane) as light yellow liquid (18%): $^1$H NMR (500 MHz, CDCl₃) δ 6.92 (2H, m, CH₃CH=CHCO, CH₂CH=CHCO), 6.25 (1H, m, CH₃CH=CHCO), 5.99 (1H, m, CH₂CH=CHCO), 3.31 (1H, m, CH3CH(CH)CO), 2.89-2.56 (1H, m, CH3CH(CH)CO, two diastereomers), 2.42 (2H, m, =CHCH₂CH₂CH), 2.03 (2H, m, =CHCH₂CH₂CH), 1.89 (3H, s, CH₃), 1.17-0.99 (3H, d, d, J=7.00 Hz, J=7.00 Hz, two diastereomers); ESI-MS: calcd for (C12H16O2Na) 215, found 215 (MNa⁺).

EXAMPLE 21

This example illustrates the preparation of Compound 21. Compound 21 was prepared by using the same method as for the preparation of Compound 19 and was obtained after purified on column (silica gel, elute: 0-10% ethyl acetate in hexane) as light yellow waxy solids (25%): $^1$H NMR (500 MHz, CDCl₃) δ 7.58 (1H, d, J=16.26 Hz, PhCH=CHCO), 7.55 (2H, m, Ar—H), 7.38 (3H, m, Ar—H), 6.98 (1H, m, CH₂CH=CHCO), 6.77 (1H, d, J=16.26 Hz, PhCH=CHCO), 6.05 (1H, m, CH₂CH=CHCO), 3.40 (1H, dd, J=17.26 Hz, J=4.62 Hz, one of PhCH=CHCOCH₂), 3.05 (1H, m, PhCH=CHCOCH₂CHCO) 2.57 (1H, dd, J=17.28 Hz, J=7.47 Hz, one of PhCH=CHCOCH₂), 2.52-2.42 (2H, m, COCH=CHCH₂CH₂), 2.17-1.08 (2H, m, COCH=CHCH₂CH₂); ESI-MS: calcd for (C16H16O2Na) 263, found 263 (MNa⁺).

EXAMPLE 22

This example illustrates the preparation of Compound 22. Compound 22 was prepared by using the same method as for the preparation of Compound 19 and was obtained after purified on column (silica gel, elute: 0-10% ethyl acetate in hexane) as orange-colored liquid (40%): $^1$H NMR (500 MHz, CDCl₃) δ 7.62 (1H, d, J=16.26 Hz, PhCH=CHCO), 7.55 (2H, m, Ar—H), 7.38 (3H, m, Ar—H), 6.98 (1H, m, CH₃CH₂CH=CHCO), 6.72 (1H, d, J=16.26 Hz, PhCH=CHCO), 6.25 (1H, m, CH₃CH₂CH=CHCO), 3.40 (1H, m, PhCH=CHCOCH₂CH(CH₃)CO), 3.24 (1H, dd, J=17.61 Hz, J=8.22 Hz, one of PhCH=CHCOCH₂), 2.66 (1H, dd, J=17.48 Hz, J=5.41 Hz, one of PhCH=CHCOCH₂), 1.93 (3H, d, J=6.89 Hz CH₃CH=CH), 1.16 (3H, d, J=7.30 Hz, CH₃CH(CH₂)CO); ESI-MS: calcd for (C16H18O2Na) 265, found 265 (MNa⁺).

EXAMPLE 23

This example illustrates the preparation of Compound 23. Compound 23 was prepared by using the same method as for the preparation of Compound 19 and was obtained after purified on column (silica gel, elute: 0-30% ethyl acetate in hexane) as orange solids (23%): $^1$H NMR (500 MHz, CDCl$_3$) δ 7.55 (1H, d, J=16.19 Hz, PhCH=CHCO), 7.13 (1H, d, J=8.31 Hz, Ar—H), 7.08 (1H, s, Ar—H), 6.98 (1H, m, CH$_2$CH=CHCO), 6.87 (1H, d, J=8.28 Hz, Ar—H), 6.66 (1H, d, J=16.22 Hz, PhCH=CHCO), 6.05 (1H, d, J=9.93 Hz, CH$_2$CH=CHCO), 3.90 (6H, s, OCH$_3$), 3.40 (1H, dd, J=17.13 Hz, J=4.52 Hz, one of PhCH=H$_2$), 3.05 (1H, m, PhCH=CHCOCH$_2$CHCO), 2.55 (1H, dd, J=17.09 Hz, J=7.65 Hz, one of PhCH=CHCOCH$_2$), 2.50-2.38 (2H, m, COCH=CHCH$_2$CH$_2$), 2.18-1.76 (2H, m, COCH=CHCH$_2$CH$_2$); ESI-MS: calcd for (C18H20O4Na) 323, found 323 (MNa$^+$).

EXAMPLE 24

This example illustrates the preparation of Compound 24. Compound 24 was prepared by using the same method as for the preparation of Compound 19 and was obtained after purified on column (silica gel, elute: 0-20% ethyl acetate in hexane) as yellow solids (35%): $^1$H NMR (500 MHz, CDCl$_3$) δ 7.50 (1H, d, J=16.13 Hz, PhCH=CHCO), 7.05 (1H, s, Ar—H), 7.03 (1H, d, J=8.06 Hz, Ar—H), 6.95 (1H, m, CH$_2$CH=CHCO), 6,82 (1H, d, J=8.02 Hz, Ar—H), 6.60 (1H, d, J=16.17 Hz, PhCH=CHCO), 6.05 (1H, d, J=10.71 Hz, CH$_2$CH=CHCO), 6.00 (2H, s, OCH$_2$O), 3.38 (1H, dd, J=17.21 Hz, J=4.57 Hz, one of PhCH=CHCOCH$_2$), 3.03 (1H, m, PhCH=CHCOCH$_2$CHCO), 2.50 (1H, dd, J=17.09 Hz, J=7.65 Hz, one of PhCH=CHCOCH$_2$), 2.45-2.38 (2H, m, COCH=CHCH$_2$CH$_2$), 1.92-1.72 (2H, m, COCH=CHCH$_2$CH$_2$); ESI-MS: calcd for (C17H16O4Na) 307, found 307 (MNa$^+$).

EXAMPLE 25

This example illustrates the preparation of Compound 25. Compound 25 was prepared by using the same method as for the preparation of Compound 19 and was obtained after purified on column (silica gel, elute: 10-50% ethyl acetate in hexane) as yellow solids (12%): $^1$H NMR (500 MHz, CDCl$_3$) δ 7.52 (1H, d, J=16.13 Hz, PhCH=CHCO), 7.40 (2H, d, J=8.06 Hz, Ar—H), 6.99 (1H, m, CH$_2$CH=CHCO), 6,89 (2H, d, J=8.02 Hz, Ar—H), 6.62 (1H, d, J=16.17 Hz, PhCH=CHCO), 6.20 (1H, s, OH), 6.05 (1H, d, J=10.71 Hz, CH$_2$CH=CHCO), 6.00 (2H, s, OCH$_2$O), 3.37 (1H, dd, J=17.21 Hz, J=4.57 Hz, one of PhCH=CHCOCH$_2$), 3.06 (1H, m, PhCH=CHCOCH$_2$CHCO), 2.50 (1H, dd, J=17.09 Hz, J=7.65 Hz, one of PhCH=CHCOCH$_2$), 2.45-2.38 (2H, m, COCH=CHCH$_2$CH$_2$), 2.17-1.78 (2H, m, COCH=CHCH$_2$CH$_2$); ESI-MS: calcd for (C16H16O3Na) 279, found 279 (MNa$^+$).

EXAMPLE 26

This example illustrates the preparation of Compound 26. Compound 26 was prepared by using the same method as for the preparation of Compound 19 and was obtained after purified on column (silica gel, elute: 0-10% ethyl acetate in hexane) as orange color solids (23%): $^1$H NMR (500 MHz, CDCl$_3$) δ 7.80 (1H, s, Ar—H), 7.72 (1H, d, J=7.98 Hz, Ar—H), 7.64 (1H, d, J=8.17 Hz, Ar—H), 7.58 (1H, d, J=16.26 Hz, PhCH=CHCO), 7.53 (1H, t, J=7.83 Hz, Ar—H), 6.98 (1H, m, CH$_2$CH=CHCO), 6.77 (1H, d, J=16.26 Hz, PhCH=CHCO), 6.05 (1H, m, CH$_2$CH=CHCO), 3.40 (1H, dd, J=17.26 Hz, J=4.62 Hz, one of PhCH=CHCOCH$_2$), 3.05 (1H, m, PhCH=CHCOCH$_2$CHCO) 2.57 (1H, dd, J=17.28 Hz, J=7.47 Hz, one of PhCH=CHCOCH$_2$), 2.52-2.42 (2H, m, COCH=CHCH$_2$CH$_2$), 2.17-1.08 (2H, m, m, COCH=CHCH$_2$CH$_2$); ESI-MS: calcd for (C17H15F3O2Na) 331, found 331 (MNa$^+$).

EXAMPLE 27

This example illustrates the preparation of Compound 27. Compound 27 was prepared by using the same method as for the preparation of Compound 19 and was obtained after purified on column (silica gel, elute: 0-25% ethyl acetate in hexane) as orange-colored syrup (15%): $^1$H NMR (500 MHz, CDCl$_3$) δ 7.59 (1H, d, J=16.28 Hz, PhCH=CHCO), 7.55 (2H, m, Ar—H), 7.40 (3H, m, Ar—H), 6.77 (1H, d, J=16.27 Hz, PhCH=CHCO), 4.16 (2H, q, J=7.15 Hz, CH$_3$CH$_2$OCO), 3.02 (2H, t, J=6.77 Hz, PhCH=CHCOCH$_2$), 2.67 (2H, t, J=6.67 Hz, PhCH=CHCOCH$_2$CH$_2$), 1.25 (3H, t, J=7.04 Hz, CH$_3$CH$_2$OCO); ESI-MS: calcd for (C14H16O3Na) 255, found 255 (MNa$^+$).

EXAMPLE 28

This example illustrates the preparation of Compound 28. A solution of trans-4-phenyl-3-butene-1-one (1.32 g) and glyoxylic acid monohydrate (0.83 g) in acetic acid (3.5 mL) was heated under reflux over night. Ethyl acetate was added and the mixture was washed by water, dried (Na$_2$SO$_4$) and concentrated. The crude product was purified by column chromatography on silica gel (elute: 0-30% ethyl acetate in hexanes) yielding in yellow solids of Compound 28 (44%): $^1$H NMR (500 MHz, CDCl$_3$) δ 7.75 (1H, d, J=16.16 Hz, PhCH=CHCO), 7.60 (2H, m, Ar—H), 7.58 (1H, d, J=15.74 Hz, HOCOCH=CHCO), 7.42 (3H, m, Ar—H), 7.00 (1H, d, J=16.05 Hz, PhCH=CHCO), 6.84 (1H, d, J=15.75 Hz, HOCOCH=CHCO); ESI-MS: calcd for (C12H10O3) 202, found 201 ([M-H]$^-$).

EXAMPLE 29

This example illustrates the preparation of Compound 29. Compound 29 was prepared by using the same method as for the preparation of Compound 28 and was obtained after purified on column (silica gel, elute: 10-50% ethyl acetate in hexane) as yellow solids (39%): $^1$H NMR (500 MHz, CDCl$_3$) δ 7.70 (1H, d, J=16.03 Hz, PhCH=CHCO), 7.58 (1H, d, J=15.69 Hz, HOCOCH=CHCO), 7.21 (1H, d, J=8.35 Hz, Ar—H), 7.12 (1H, s, Ar—H), 6.90 (1H, d, J=8.34 Hz, Ar—H), 6.86 (1H, d, J=16.21 Hz, PhCH=CHCO), 6.83 (1H, d, J=15.82 Hz, HOCOCH=CHCO), 3.94 (6H, s, OCH$_3$); ESI-MS: calcd for (C14H14O5) 262, found 261 ([M−H]$^-$).

EXAMPLE 30

This example illustrates the preparation of Compound 30. Compound 30 was prepared by using the same method as for the preparation of Compound 28 and was obtained after purified on column (silica gel, elute: 10-50% ethyl acetate in hexane) as yellow solids (79%): $^1$H NMR (500 MHz, CDCl$_3$) δ 7.65 (1H, d, J=16.00 Hz, PhCH=CHCO), 7.58 (1H, d, J=15.69 Hz, HOCOCH=CHCO), 6.88 (1H, d, J=16.08 Hz, PhCH=CHCO), 6.84 (1H, d, J=15.77 Hz, HOCOCH=CHCO), 6.83 (2H, s, Ar—H), 3.90 (9H, m, 3×OCH$_3$); ESI-MS: calcd for (C15H16O6) 292, found 291 ([M-H]$^-$).

EXAMPLE 31

This example illustrates the preparation of Compound 31. To a solution of Compound 28 (0.17 g, 0.84 mmol) in dichloromethane (10 mL) was added ethanol (0.15 mL 2.56 mmol), N-(3-dimethylaminopropyl)-N'ethylcarbodiimide hydrochloride (0.20 g, 1.05 mmol) and DMAP (cat.) and the reaction was stirred at room temperature overnight. The mixture was washed by dilute HCl (~0.02N), water, dried ($Na_2SO_4$) and concentrated. The crude product was purified by column chromatography on silica gel (0-10% ethyl acetate in hexanes) to give red solids of the desired product (0.075 g, 39%): $^1$H NMR (500 MHz, $CDCl_3$) δ 7.72 (1H, d, J=16.16 Hz, PhC$\underline{H}$=CHCO), 7.60 (2H, m, Ar—$\underline{H}$), 7.48 (1H, d, J=15.74 Hz, HOCOC$\underline{H}$=CHCO), 7.44 (3H, m, Ar—$\underline{H}$), 7.00 (1H, d, J=16.05 Hz, PhC$\underline{H}$=CHCO), 6.84 (1H, d, J=15.75 Hz, HOCOCH=C$\underline{H}$CO), 4.30 (2H, q, J=7.27 Hz, OC$\underline{H}_2CH_3$), 1.35 (3H, t, J=7.24 Hz, $OCH_2C\underline{H}_3$); ESI-MS: calcd for (C14H14O3Na) 253, found 253 MNa$^+$).

EXAMPLE 32

This example illustrates the preparation of Compound 32. To a solution of Compound 28 (0.15 g, 0.74 mmol) in dichloromethane (10 mL) was added N-methylpropylamine (0.15 mL, 1.48 mmol), HOBt (0.15 g, 1.11 mmol), $Et_3N$ (0.21 mL, 1.48 mmol) and EDC (0.19 g, 1.48 mmol) at 0° C. and the mixture was stirred at room temperature overnight. 1N HCl was added and the mixture was extracted with dichloromethane. The combined organic layer was washed by sodium bicarbonate, brine, dried ($Na_2SO_4$) and concentrated. The crude product was purified by column chromatography on silica gel (10-50% ethyl acetate in hexanes) to give light yellow oil of the desired product (0.15 g, 78%): $^1$H NMR (500 MHz, $CDCl_3$) δ 7.75 (1H, d, J=16.16 Hz, PhC$\underline{H}$=CHCO), 7.58 and 7.42 (3H+4H, m, m 5×Ar—$\underline{H}$, NCOC$\underline{H}$=CHCO, NCOCH=C$\underline{H}$CO), 6.91 (1H, d, J=16.23 Hz, PhCH=C$\underline{H}$CO), 3.45 and 3.39 (2H, t, t, J=7.45 Hz, J=7.39 Hz, for two isomers, $CH_3NC\underline{H}_2CH_2CH_3$), 3.13 and 3.05 (3H, s, s, C$\underline{H}_3NCH_2CH_2CH_3$), 1.62 (2H, m, CH3NCH2C$\underline{H}$2CH3), 0.94 (3H, t, J=7.36 Hz, $CH_3NCH_2CH_2C\underline{H}_3$); ESI-MS: calcd for (C16H19NO2Na) 280, found 280 (MNa$^+$).

EXAMPLE 33

This example illustrates the preparation of Compound 33. To a solution of Compound 28 (0.10 g, 0.49 mmol) in toluene (15 mL) was added oxalyl chloride (0.15 mL, 1.48 mmol), HOBt (0.15 g, 1.11 mmol), $Et_3N$ (0.21 mL, 1.48 mmol) and EDC (0.10 ml, 1.16 mmol) at room temperature and the mixture was stirred at room for 2 hours. The solvents were removed under reduced pressure. The residue was dissolved in dichloromethane and triethylamine was added, followed by aniline at 0° C. The mixture was stirred overnight at room temperature. 1N HCl was added and the mixture was extracted with dichloromethane. The combined organic layer was washed by sodium bicarbonate, brine, dried ($Na_2SO_4$) and concentrated. The crude product was purified by column chromatography on silica gel (0-15% ethyl acetate in hexanes) to give dark solids (5%): ESI-MS: calcd for (C18H15NO2) 277, found 276 ([M-H]$^-$).

EXAMPLE 34

This example illustrates the preparation of Compound 34. Compound 34 was prepared by using the same method as for the preparation of Compound 32 and used Compound 29 as the starting material. Compound 34 was obtained after purified on column (silica gel, elute: 20-75% ethyl acetate in hexane) as orange oil (83%): $^1$H NMR (500 MHz, $CDCl_3$) δ 7.70 (1H, d, J=16.15 Hz, PhC$\underline{H}$=CHCO), 7.58 (1H, d, J=14.92, NCOC$\underline{H}$=CHCO), 7.38 (1H, d, J=15.00, NCOCH=C$\underline{H}$CO), 7.18 (1H, d, J=8.29 Hz, Ar—$\underline{H}$), 7.10 (1H, s, Ar—$\underline{H}$), 6.89 (1H, d, J=8.33 Hz, Ar—$\underline{H}$), 6.78 (1H, d, J=16.19 Hz, PhCH=C$\underline{H}$CO), 3.93 (6H, s, 2×OC$\underline{H}_3$), 3.45 and 3.39 (2H, t, t, J=7.50 Hz, J=7.40 Hz, for two isomers, $CH_3NC\underline{H}_2CH_2CH_3$), 3.13 and 3.05 (3H, s, s, C$\underline{H}_3NCH_2CH_2CH_3$), 1.62 (2H, m, CH3NCH2C$\underline{H}$2CH3), 0.94 (3H, t, J=7.36 Hz, $CH_3NCH_2CH_2C\underline{H}_3$); ESI-MS: calcd for (C18H23NO4Na) 340, found 340 (MNa$^+$).

EXAMPLE 35

This example illustrates the preparation of Compound 35. Compound 35 was prepared by using the same method as for the preparation of Compound 32 and used Compound 29 as the starting material. Compound 35 was obtained after purified on column (silica gel, elute: 10-50% ethyl acetate in hexane) as orange solids (28%): $^1$H NMR (500 MHz, $CDCl_3$) δ 7.99 (1H, s, NH), 7.75-7.65 (4H, m, PhC$\underline{H}$=CHCO, NCOC$\underline{H}$=CHCO, NCOCH=C$\underline{H}$CO, 1×Ar—$\underline{H}$), 7.35 (2H, m, 2×Ar—$\underline{H}$), 7.20-7.05 (4H, m, 4×Ar—$\underline{H}$), 6.89 (1H, d, J=8.33 Hz, 1×Ar—$\underline{H}$), 6.85 (1H, d, J=16.09 Hz, PhCH=C$\underline{H}$CO), 3.93 (6H, s, 2×OC$\underline{H}_3$); ESI-MS: calcd for (C20H19NO4Na) 360, found 360 (MNa$^+$).

EXAMPLE 36

This example illustrates the preparation of Compound 36. Compound 36 was prepared by using the same method as for the preparation of Compound 32 and used Compound 29 as the starting material. Compound 36 was obtained after purified on column (silica gel, elute: MeOH/$Et_3$N/EtOAc: Feb. 2, 1996) as yellow oil (46%): $^1$H NMR (500 MHz, $CDCl_3$) δ 7.70 (1H, d, J=16.15 Hz, PhC$\underline{H}$=CHCO), 7.56 (1H, d, J=14.92, NCOC$\underline{H}$=CHCO), 7.38 (1H, d, J=15.00, NCOCH=C$\underline{H}$CO), 7.18 (1H, d, J=8.29 Hz, Ar—$\underline{H}$), 7.10 (1H, s, Ar—$\underline{H}$), 6.89 (1H, d, J=8.33 Hz, Ar—$\underline{H}$), 6.78 (1H, d, J=16.19 Hz, PhCH=C$\underline{H}$CO), 3.95 (6H, s, 2×OC$\underline{H}_3$), 3.80-3.70 (4H, br, C$\underline{H}_2$N(CO)C$\underline{H}_2$), 2.51 (4H, br, C$\underline{H}_2$N($CH_3$)C$\underline{H}_2$), 2.37 (3H, s, C$\underline{H}_3$); ESI-MS: calcd for (C19H24N2O4) 344, found 345 (MH$^+$).

EXAMPLE 37

This example illustrates the preparation of Compound 37. Compound 37 was prepared by using the same method as for the preparation of Compound 32 and used Compound 29 as the starting material. Compound 37 was obtained after purified on column (silica gel, elute: MeOH/$Et_3$N/EtOAc: Feb. 2, 1996) as red solids (21%): $^1$H NMR (500 MHz, $CDCl_3$) δ 8.30 (2H, d, J=5.43 Hz, 2×Py-$\underline{H}$), 7.72 (1H, d, J=16.15 Hz, PhC$\underline{H}$=CHCO), 7.63 (1H, d, J=14.91 Hz, NCOC$\underline{H}$=CHCO), 7.40 (1H, d, J=14.90 Hz, NCOCH=C$\underline{H}$CO), 7.19 (1H, d, J=8.34 Hz, Ar—$\underline{H}$), 7.11 (1H, s, Ar—$\underline{H}$), 6.90 (1H, d, J=8.37 Hz, Ar—$\underline{H}$), 6.82 (1H, d, J=16.14 Hz, PhCH=C$\underline{H}$CO), 6.74 (2H, d, J=6.56 Hz, 2×Py-$\underline{H}$), 3.94 (6H, s, 2×OC$\underline{H}_3$), 3.91-3.74 (4H, br, C$\underline{H}_2$N(CO)C$\underline{H}_2$), 3.51 (4H, br, C$\underline{H}_2$N(Py)C$\underline{H}_2$); ESI-MS: calcd for (C23H25N3O4) 407, found 408 (MH$^+$).

EXAMPLE 38

This example illustrates the preparation of Compound 38. Compound 38 was prepared by using the same method as for the preparation of Compound 32 and used Compound 29 as the starting material. Compound 38 was obtained after purified on column (silica gel, elute: 10-50% ethyl acetate in hexanes) as red solids (32%): $^1$H NMR (500 MHz, CDCl$_3$) δ 7.72 (1H, d, J=16.15 Hz, PhC$\underline{H}$=CHCO), 7.62 (1H, d, J=14.91 Hz, NCOC$\underline{H}$=CHCO), 7.45 (1H, d, J=14.90 Hz, NCOCH=C$\underline{H}$CO), 7.35-6.83 (8H, m, Ar—$\underline{H}$), 6.82 (1H, d, J=16.14 Hz, PhCH=C$\underline{H}$CO), 3.95 (6H, s, 2×OC$\underline{H}_3$), 3.91-3.78 (4H, br, C$\underline{H}_2$N(CO)C$\underline{H}_2$), 3.23 (4H, br, C$\underline{H}_2$N(Ph)C$\underline{H}_2$); ESI-MS: calcd for (C23H25N3O4) 407, found 408 (MH$^+$).

EXAMPLE 39

This example illustrates the preparation of Compound 39. Compound 39 was prepared by using the same method as for the preparation of Compound 32 and used Compound 30 as the starting material. Compound 39 was obtained after purified on column (silica gel, elute: MeOH/Et$_3$N/EtOAc: May 2, 1995) as yellow syrup (70%): $^1$H NMR (500 MHz, CDCl$_3$) δ 7.65 (1H, d, J=16.15 Hz, PhC$\underline{H}$=CHCO), 7.54 (1H, d, J=15.00, NCOC$\underline{H}$=CHCO), 7.38 (1H, d, J=15.09, NCOCH=C$\underline{H}$CO), 6.81 (2H, s, Ar—$\underline{H}$), 6.82-6.80 (1H, d, J=16.18 Hz, PhCH=C$\underline{H}$CO), 3.89-3.85 (9H, m, 3×OC$\underline{H}_3$), 3.75-3.61 (4H, br, C$\underline{H}_2$N(CO)C$\underline{H}_2$), 2.44 (4H, br, C$\underline{H}_2$N(CH$_3$)C$\underline{H}_2$), 2.33 (3H, s, C$\underline{H}_3$); ESI-MS: calcd for (C20H26N2O5) 374, found 375 (MH$^+$).

EXAMPLE 40

This example illustrates the preparation of Compound 40. Compound 40 was prepared by using the same method as for the preparation of Compound 32 and used Compound 30 as the starting material. Compound 40 was obtained after purified on column (silica gel, elute: MeOH/Et$_3$N/EtOAc: May 2, 1995) as orange solids (31%): $^1$H NMR (500 MHz, CDCl$_3$) δ 8.33 (2H, d, J=6.41 Hz, 2×Py-$\underline{H}$), 7.68 (1H, d, J=16.15 Hz, PhC$\underline{H}$=CHCO), 7.63 (1H, d, J=15.04 Hz, NCOC$\underline{H}$=CHCO), 7.42 (1H, d, J=14.89 Hz, NCOCH=C$\underline{H}$CO), 6.84 (1H, d, J=16.04 Hz, PhCH=C$\underline{H}$CO), 6.82 (2H, s, Ar—$\underline{H}$), 6.68 (2H, d, J=6.50 Hz, 2×Py-$\underline{H}$), 3.90 (9H, m, 3×OC$\underline{H}_3$), 3.88-3.76 (4H, br, C$\underline{H}_2$NCO)), 3.44-3.40 (4H, br, C$\underline{H}_2$N(Py)C$\underline{H}_2$); ESI-MS: calcd for (C24H27N3O5) 437, found 438 (MH$^+$).

EXAMPLE 41

This example illustrates the preparation of Compound 41. To a solution of N-(fluorophenyl)malemic acid (0.30 g, 1.43 mmol) in dichloromethane (50 mL) was added methanol (3 mL, 74.07 mmol), N-(3-dimethylaminopropyl)-N'ethylcarbodiimide hydrochloride (0.34 g, 1.78 mmol) and DMAP (0.0175 g, 0.143 mmol) and the reaction was stirred at room temperature overnight. The mixture was washed by dilute HCl (~0.02N), water, dried (Na$_2$SO$_4$) and concentrated. The crude product was purified by column chromatography on silica gel (10-30% ethyl acetate in hexanes) to give light yellow solids of the desired product (28%): $^1$H NMR (500 MHz, CDCl$_3$) δ 10.94 (1H, s, NH), 7.63 (2H, m, Ar—$\underline{H}$), 7.04 (2H, m, Ar—$\underline{H}$), 6.44 (1H, d, J=13.4, PhC$\underline{H}$=CH), 6.23 (1H, d, J=13.4, PhCH=C$\underline{H}$), 3.86 (3H, s, C$\underline{H}_3$OCO); ESI-MS: calcd for (C11H10FNO3Na) 246, found 246 (MNa$^+$).

EXAMPLE 42

This example illustrates the preparation of Compound 42. To a solution of Compound 23 (100 mg, 0.33 mmol) in pyridine/acetic acid (5/1) was added methoxyaminehydrochloride (0.56 g, 6.66 mmol) at room temperature and stirred at 40° C. for 2 hours. 1N HCl was added and the mixture was extracted by ethyl acetate three times. The combined organic was washed by brine, dried (Na$_2$SO4) and concentrated. The crude product was purified on silica gel column, using 0-20% ethyl acetate in hexane as the eluting solvents. The desired product was obtained as colorless oil of isomers mixture (120 mg, 100%): $^1$H NMR (500 MHz, CDCl$_3$) δ 7.20-6.07 (7H, m, Ar—$\underline{H}$, C$\underline{H}$of all alkenes), 4.00-3.87 (12H, s, 4×OC$\underline{H}_3$), 3.57-2.42 (3H, m, PhCH=CHCOC$\underline{H}_2$, PhCH=CHCOCH$_2$C$\underline{H}$CO), 2.38-1.66 (4H, m, COCH=CHC$\underline{H}_2$C$\underline{H}_2$); ESI-MS: calcd for (C20H26N2O4Na) 381, found 381 (MNa$^+$).

EXAMPLE 43

This example illustrates the preparation of Compounds 43 and 44. Compounds 43 and 44 were prepared by using the same method as for the preparation of Compound 42 and used Compound 32 as the starting material. Two isomers were obtained and separated by column on silica gel (0-20% ethyl acetate in hexane) as colorless oil. Compound 43 (45%): $^1$H NMR (500 MHz, CDCl$_3$) δ 7.54 (1H, d, J=16.00 Hz, PhC$\underline{H}$=CHCO), 7.46 (2H, m, Ar—$\underline{H}$), 7.36 (2H, t, J=7.11 Hz, Ar—$\underline{H}$), 7.29 (1H, t, J=8.58 Hz, Ar—$\underline{H}$), 7.00 (1H, overlap of two d, J=16.00, J=16.00, due to two config. isomers regarding to amide, NCOC$\underline{H}$=CHCO), 6.87 (1H, d, J=15.94, NCOCH=C$\underline{H}$CO), 6.80 (1H, d, J=16.00 Hz, PhCH=C$\underline{H}$CO), 4.00 and 3.99 (3H, s, s, OC$\underline{H}_3$, due to two config. isomers regarding to amide) 3.45 and 3.39 (2H, t, t, J=7.45 Hz, J=7.36 Hz, CH$_3$NC$\underline{H}_2$CH$_2$CH$_3$, due to two config. isomers regarding to amide), 3.07 and 3.04 (3H, s, s, C$\underline{H}_3$NCH$_2$CH$_2$CH$_3$, due to two config. isomers regarding to amide), 1.62 (2H, m, CH$_3$NCH$_2$C$\underline{H}$2CH$_3$), 0.94 (3H, t, J=7.36 Hz, CH$_3$NCH$_2$CH$_2$C$\underline{H}_3$); ESI-MS: calcd for (C17H22N2O2Na) 309, found 309 (MNa$^+$). Compound 44 (26%): $^1$H NMR (500 MHz, CDCl$_3$) δ 7.50 (2H, m, PhC$\underline{H}$=CHCO, 1×Ar—$\underline{H}$), 7.46 (1H, d, J=15.24 Hz, NCOC$\underline{H}$=CHCO), 7.34 (4H, m, 4×Ar—$\underline{H}$), 7.00 (1H, overlap of two d, J=16.85, J=16.82, due to two config. isomers regarding to amide, PhCH=C$\underline{H}$CO), 6.78 (1H, overlap of two d, J=15.39, due to two config. isomers regarding to amide, NCOCH=C$\underline{H}$CO), 4.03 (3H, s, s, OC$\underline{H}_3$, 3.45 and 3.39 (2H, t, t, J=7.45 Hz, J=7.36 Hz, due to two config. isomers regarding to amide, CH$_3$NC$\underline{H}_2$CH$_3$), 3.11 and 3.04 (3H, s, s, due to two config. isomers regarding to amide, C$\underline{H}_3$NCH$_2$CH$_2$CH$_3$), 1.62 (2H, m, CH3NCH2C$\underline{H}$2CH$_3$), 0.94 (3H, t, J=7.36 Hz, CH$_3$NCH$_2$CH$_2$C$\underline{H}_3$); ESI-MS: calcd for (C17H22N2O2Na) 309, found 309 (MNa$^+$).

EXAMPLE 44

This example illustrates the preparation of Compound 45. Compound 45 was prepared by using the same method as for the preparation of Compound 42 and used Compound 36 as the starting material. A mixture of two isomers was obtained and purified on column (silica gel, 0-10% TEA in ethyl acetate) as light-yellow solids (10%): $^1$H NMR (500 MHz, CDCl$_3$) δ 7.56-7.48 (2H, obscured two d, J=16.00 Hz, J=15.27 Hz, PhC$\underline{H}$=CHCOCH=CHCON, cis and trans), 7.29 (1H, d, J=16.73 Hz, PhCH=C$\underline{H}$COCH=CHCON, cis or trans), 7.08-6.70 (10H, m, PhCH=CHCOC$\underline{H}$=C$\underline{H}$CON, Ph-$\underline{H}$, cis and trans), 6.67 (1H, d, J=16.35 Hz, PhCH=CHCOC$\underline{H}$=CHCON, cis or trans), 3.91-3.88 (12H, m, OCH$_3$, cis and trans), 3.81-3.61 (8H, m, C$\underline{H}_2$NCO, cis and trans), 2.45 (8H, m, CH$_3$NCH2, cis and trans), 2.30 (6H, s, C$\underline{H}_3$N); ESI-MS: calcd for (C19H25N3O4) 359, found 360 (MH$^+$).

EXAMPLE 45

This example illustrates the preparation of Compound 46. Compound 46 was prepared by using the same method as for the preparation of Compound 42 and used Compound 36 as the starting material. A mixture of two isomers was obtained and purified on column (silica gel, 0-5% TEA in ethyl acetate) as light-yellow waxy solids (64%): $^1$H NMR (500 MHz, CDCl$_3$) δ 7.49-7.45 (2H, obscured two d, J=15.92 Hz, J=15.25 Hz, PhC$\underline{H}$=CHCOCH=CHCON, cis and trans), 7.15 (1H, d, J=16.74 Hz, PhCH=C$\underline{H}$COCH=CHCON, cis or trans), 7.08-6.70 (10H, m, PhCH=CHCOC$\underline{H}$=CHCON, Ph-H, cis and trans), 6.67 (1H, d, J=15.39 Hz, PhCH=C$\underline{H}$COCH=CHCON, cis or trans), 4.03 and 3.98 (6H, s, s, NOC$\underline{H}_3$, cis and trans), 3.92-3.88 (12H, m, OCH$_3$, cis and trans), 3.75-3.46 (8H, m, C$\underline{H}_2$NCO, cis and trans), 2.43 (8H, m, CH$_3$NC$\underline{H}_2$, cis and trans), 2.31 (6H, s, C$\underline{H}_3$N); ESI-MS: calcd for (C20H27N3O4) 373, found 374 (MH$^+$).

EXAMPLE 46

This example illustrates the preparation of Compound 47. Compound 47 was prepared by using the same method as for the preparation of Compound 42 and used Compound 36 as the starting material. A mixture of two isomers was obtained and purified on column (silica gel, 0-5% TEA in ethyl acetate) as light-yellow syrups (71%): $^1$H NMR (500 MHz, CDCl$_3$) δ 7.67 (1H, d, J=16.16 Hz, PhC$\underline{H}$=CHCOCH=CHCON, cis or trans), 7.58 (1H, d, J=15.24 Hz, PhC$\underline{H}$=CHCOCH=CHCON, cis or trans), 7.40-6.80 (22H, m, PhCH=CHCOC$\underline{H}$=C$\underline{H}$CON, Ph-$\underline{H}$, cis and trans), 3.95-3.91 (12H, s, s, s, s, OCH$_3$, cis and trans), 3.78-3.61 (8H, m, C$\underline{H}_2$NCO, cis and trans), 2.45 (8H, m, CH$_3$NC$\underline{H}$2, cis and trans), 2.32 (6H, s, C$\underline{H}_3$N); ESI-MS: calcd for (C25H29N3O4Na) 458, found 458 (MNa$^+$).

EXAMPLE 47

This example illustrates the preparation of Compound 48. Compound 48 was prepared by using the same method as for the preparation of Compound 42 and used Compound 36 as the starting material. A mixture of two isomers was obtained and purified on column (silica gel, 0-5% TEA in ethyl acetate) as light-yellow syrups (71%): $^1$H NMR (500 MHz, CDCl$_3$) δ 7.48-6.67 (24H, m, PhC$\underline{H}$=C$\underline{H}$COC$\underline{H}$=C$\underline{H}$CON, Ph-$\underline{H}$, cis and trans), 5.27 and 5.22 (4H, s, s PhC$\underline{H}_2$, cis and trans), 3.90-3.89 (12H, m, OCH$_3$, cis and trans), 3.78-3.47 (8H, m, C$\underline{H}_3$NCO, cis and trans), 2.42 (8H, m, CH$_3$NC$\underline{H}_2$, cis and trans), 2.32 and 2.29 (6H, s, s, C$\underline{H}_3$N); ESI-MS: calcd for (C26H31N3O4) 449, found 450 (MH$^+$).

EXAMPLE 48

This example illustrates the preparation of Compound 49. Compound 49 was prepared by using the same method as for the preparation of Compound 42 and used Compound 39 as the starting material. A mixture of two isomers was obtained and purified on column (silica gel, 0-5% TEA in ethyl acetate) as light-yellow waxy solids (55%): $^1$H NMR (500 MHz, CDCl$_3$) δ 7.48-7.43 (2H, obscured two d, J=16.00 Hz, PhC$\underline{H}$=CHCOCH=CHCON, cis and trans), 7.18-6.73 (6H, m, PhCH=C$\underline{H}$COC$\underline{H}$=C$\underline{H}$CON, cis and trans), 6.70 (2H, s, Ar—$\underline{H}$, cis and trans), 6.67 (2H, s, Ar—$\underline{H}$, cis and trans), 4.03 and 4.00 (6H, s, s, NOC$\underline{H}_3$, cis and trans), 3.89-3.85 (18H, m, OCH$_3$, cis and trans), 3.75-3.48 (8H, m, C$\underline{H}_2$NCO, cis and trans), 2.43 (8H, m, CH$_3$NC$\underline{H}_2$, cis and trans), 2.30 (6H, s, C$\underline{H}_3$N); ESI-MS: calcd for (C21H29N3O5) 403, found 404 (MH$^+$).

EXAMPLE 49

This example illustrates the preparation of Compound 50. To a solution of hydroxylamine hydrochloride (1.45 g, 21 mmol) in 70 mL of 1:1 t-BuOH:H$_2$O was added trans-Cinnamaldehyde (2.5 mL, 20 mmol). To this was added NaOH (21 mL of 1M solution, 21 mmol), and after being stirred for 30 min at ambient temperature, TLC analysis indicated that oxime formation was complete. Chloramine-T trihydrate (5.88 g, 21 mmol) was added in small portions over 5 min, followed by CuSO$_4$.5H$_2$O (0.25 g, 1.0 mmol) and copper turnings (ca. 90 mg). Propiolic acid, (1.30 mL, 21 mmol) and sodium bicarbonate (1.8 g, 21 mmol) was added cocurrently. pH was adjusted to ca. 6 by addition of a few drops of 1 M NaOH, and stirring was continued for overnight. The reaction mixture was poured into ice/water (150 mL), and 1N HCl was added to adjust the PH~2. The product was collected by filtration, redissolved, and passed through a short plug of silica gel (50-100% ethyl acetate in hexanes) affording an off-white solid of the desired product (3%): $^1$H NMR (500 MHz, DMSO-d$_6$): δ 7.67-7.57 (4H, m), 7.46-7.30 (3H, m), 7.27 (1H, d, J=16.76 Hz); ESI-MS: calcd for (C12H9NO3) 215, found 214 ([M-H]$^-$).

EXAMPLE 50

This example illustrates the preparation of Compound 51. Compound 51 was prepared by using the same method as for the preparation of Compound 50. After purified on column (silica gel, 0-5% ethyl acetate in hexanes), Compound 51 was obtained as white solids (21%): $^1$H NMR (500 MHz, CDCl$_3$): δ 7.53 (2H, d, J=8.50 Hz, Ar—$\underline{H}$), 7.41-7.35 (3H, m, Ar—$\underline{H}$), 7.23 (1H, d, J=16.58 Hz, C$\underline{H}$=CH), 7.18 (1H, s, C$\underline{H}$), 7.15 (1H, d, J=16.58 Hz, CH=C$\underline{H}$), 4.45 (2H, q, J=7.01 Hz, C$\underline{H}_2$CH$_3$), 1.43 (3H, t, J=7.33 Hz, CH$_2$C$\underline{H}_3$); ESI-MS: calcd for (C14H13NO3) 243, found 244 (MH$^+$).

EXAMPLE 51

This example illustrates the preparation of Compound 52. Following the amide synthesis method such as the method used in the preparation of Compound 32, from Compound 50, the desired product was prepared and purified on column (silica gel, 0-25% ethyl acetate in hexanes) as white solids (18%): $^1$H NMR (500 MHz, CDCl$_3$): δ 7.55 (2H, d, J=7.28 Hz, Ar—$\underline{H}$), 7.50-7.30 (3H, m, Ar—$\underline{H}$), 7.22 (1H, d, J=16.64 Hz, C$\underline{H}$=CH), 7.11 (1H, d, J=16.56 Hz, CH=C$\underline{H}$), 7.00 and 6.98 (1H, s, s, C$\underline{H}$cis and trans), 3.51 (2H, t, J=7.53 Hz, NC$\underline{H}_2$CH$_2$CH$_3$), 3.24 and 3.10 (3H, s, s, NC$\underline{H}_3$), 1.88-1.71 (2H, m, NCH$_2$C$\underline{H}_2$CH$_3$), 0.99 and 0.92 (3H, t, t, J=7.42 Hz, J=7.43 Hz, NCH$_2$CH$_2$C$\underline{H}_3$); ESI-MS: calcd for (C16H18N2O2) 270, found 93 (MNa$^+$).

EXAMPLE 52

In Vitro Evaluation

This example showed the in vitro growth inhibition experiments for the compounds in the invention on MX-1 (human breast carcinoma) cells. The cytotoxicity assay was quantitated using the Promega CellTiter Blue Cell Viability Assay. Briefly, cells (5000 cells/well) were plated onto 96-well microtiter plates in RPMI 1640 medium supplemented with 10% FBS and incubated at 378 C in a humidified 5% CO$_2$ atmosphere. After 24 h, cells were exposed to various concentrations of compound in DMSO and cultured for another 72 h. 100 ul of media were removed and 20 ul of Promega CellTiter Blue reagent were added to each well and shaken to mix. After 4 hours of incubation at 37° C. in a humidified 5% CO2 atmosphere, the plates were read at 544 ex/620 em. The fluorescence produced is proportional to the number of viable cells. After plotting fluorescence produced against drug concentration, the $IC_{50}$ was calculated as the half-life of the resulting non-linear regression. The data showed in Table 1.

TABLE 1

$IC_{50}$ dicarbonyl derivatives

| ID | Chemical Structure | $IC_{50}(\mu M)$ |
|----|---|---|
| 1 | 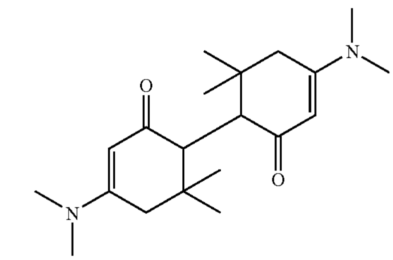 | >1000 |
| 2 | 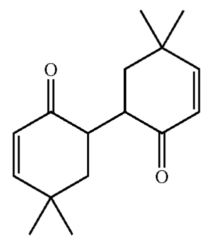 | 56.83 |
| 3 | 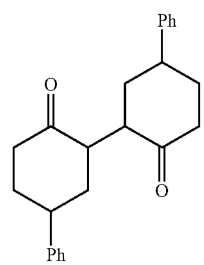 | 29.73 |
| 4 | 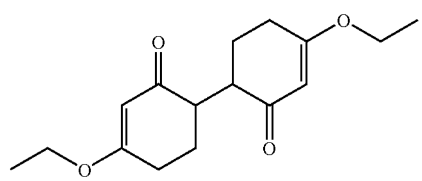 | >1000 |
| 5 | 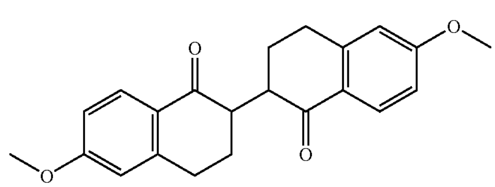 | >1000 |
| 6 | 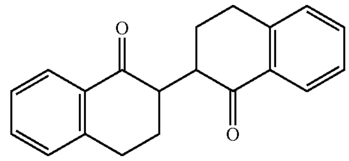 | >1000 |

TABLE 1-continued

IC$_{50}$ dicarbonyl derivatives

| ID | Chemical Structure | IC$_{50}$(μM) |
| --- | --- | --- |
| 7 | 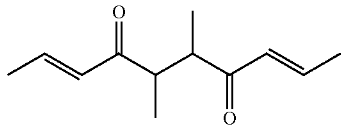 | 2.63 |
| 8 | 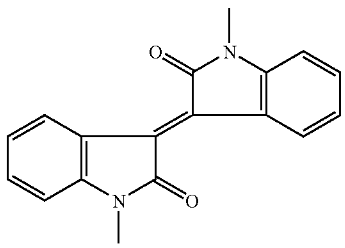 | 351.68 |
| 9 | 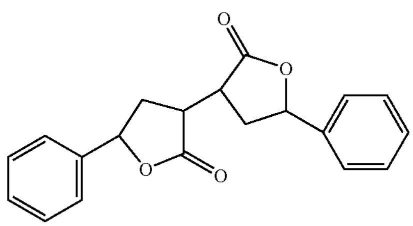 | 472.47 |
| 10 | 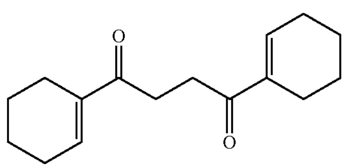 | >1000 |
| 11 | 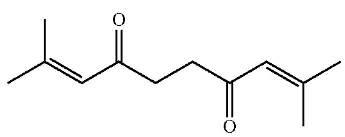 | 10.29 |
| 12 | 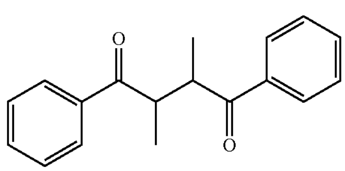 | >1000 |
| 13 | 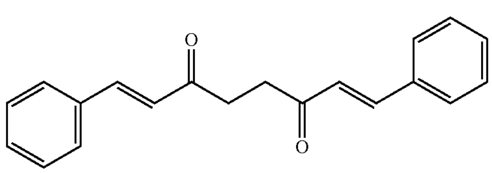 | 37.88 |
| 14 | 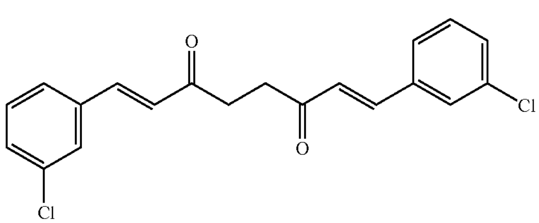 | 55.67 |

TABLE 1-continued

IC$_{50}$ dicarbonyl derivatives

| ID | Chemical Structure | IC$_{50}$(µM) |
|---|---|---|
| 15 | 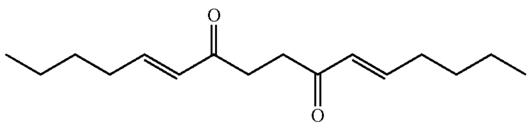 | 7.99 |
| 16 | 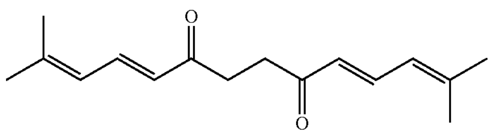 | 16.24 |
| 17 | 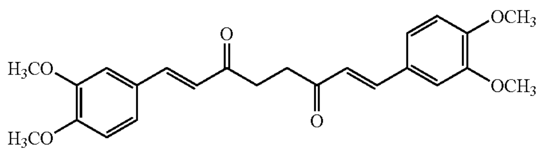 | 73.09 |
| 18 | 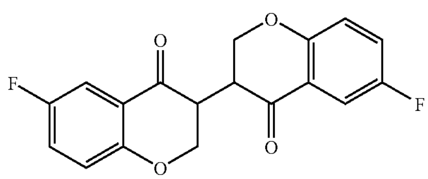 | >1000 |
| 19 | 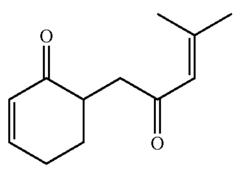 | 1.04 |
| 20 | 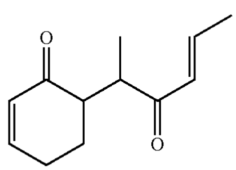 | 0.52 |
| 21 | 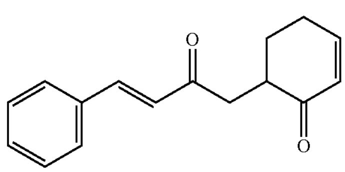 | 0.42 |
| 22 | 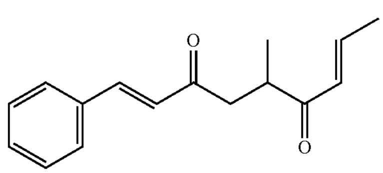 | 2.07 |
| 23 | 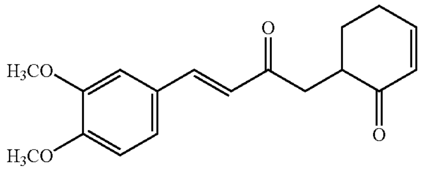 | 0.17 |

TABLE 1-continued
IC$_{50}$ dicarbonyl derivatives
| ID | Chemical Structure | IC$_{50}$(μM) |
|---|---|---|
| 24 | 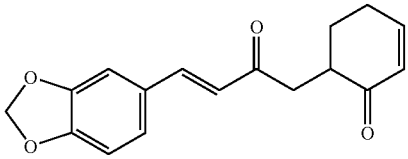 | 0.70 |
| 25 | 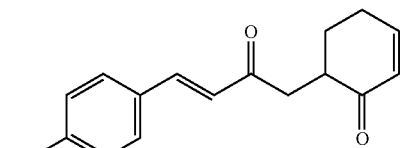 | 0.16 |
| 26 | 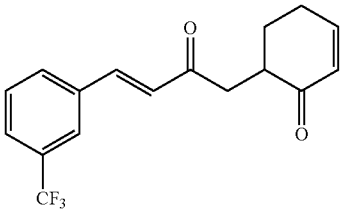 | 2.59 |
| 27 | 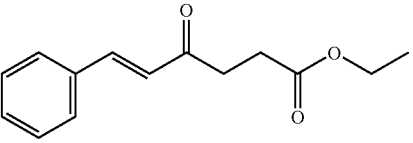 | 77.49 |
| 28 | 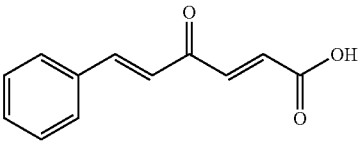 | 3.96 |
| 29 | 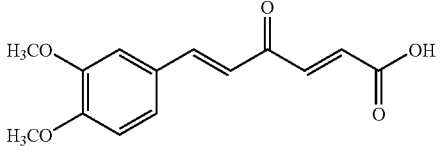 | 29.00 |
| 30 | 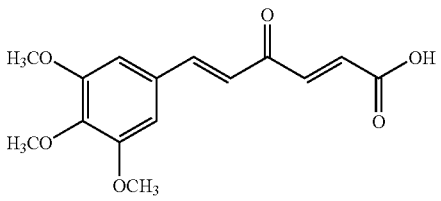 | 34.21 |
| 31 | 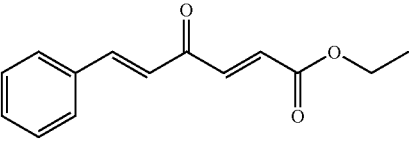 | 2.17 |

TABLE 1-continued

IC$_{50}$ dicarbonyl derivatives

| ID | Chemical Structure | IC$_{50}$(μM) |
|---|---|---|
| 32 | 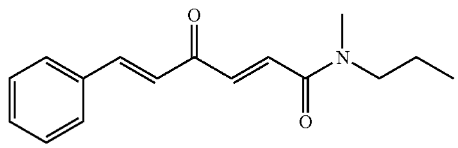 | 0.39 |
| 33 | 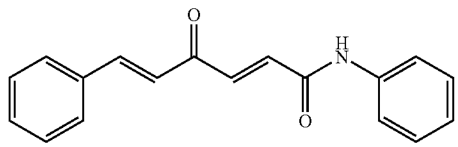 | 3.25 |
| 34 | 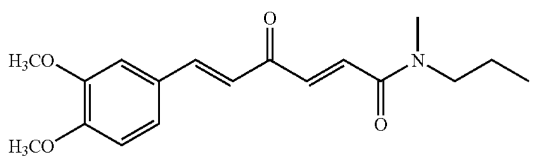 | 0.28 |
| 35 | 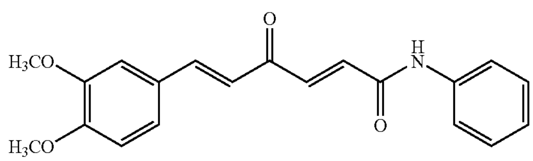 | 0.89 |
| 36 | 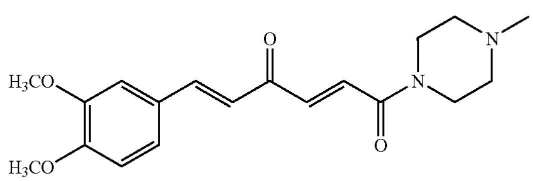 | 0.17 |
| 37 | 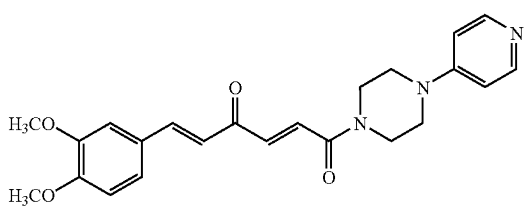 | 0.12 |
| 38 | 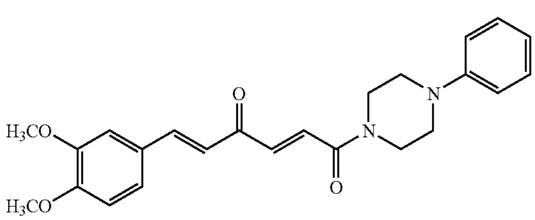 | 0.25 |
| 39 | 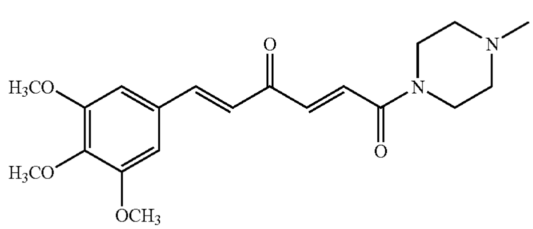 | 0.80 |

TABLE 1-continued

IC$_{50}$ dicarbonyl derivatives

| ID | Chemical Structure | IC$_{50}$(μM) |
|---|---|---|
| 40 | 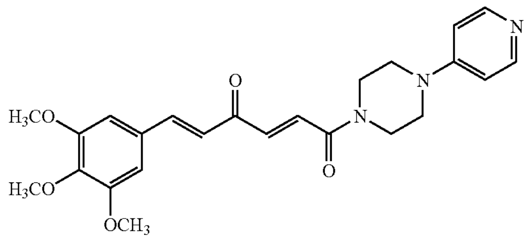 | 0.48 |
| 41 | 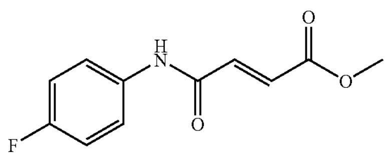 | 120.97 |
| 42 | 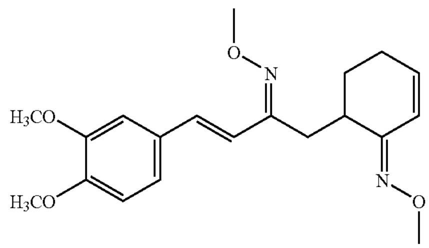 | 128.34 |
| 43 | 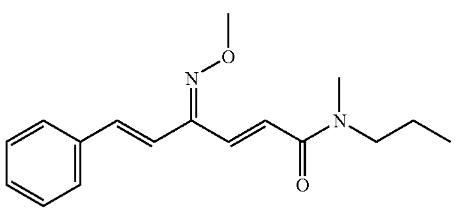 | 171.11 |
| 44 | 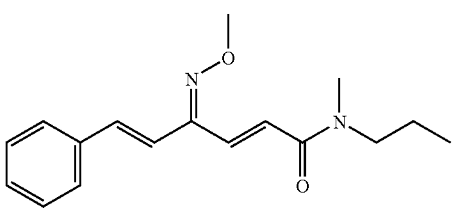 | 171.11 |
| 45 | 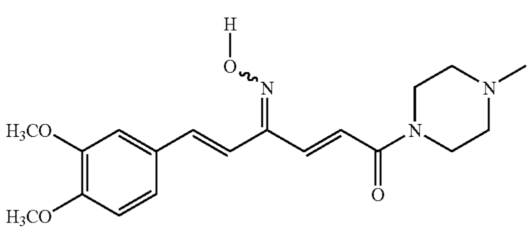 | 371.15 |
| 46 | 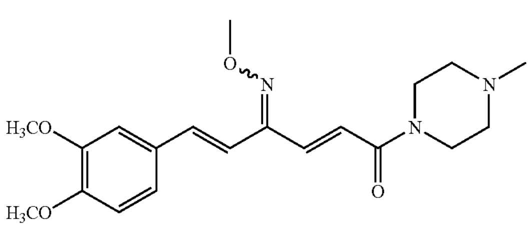 | 481.99 |

TABLE 1-continued
IC$_{50}$ dicarbonyl derivatives
| ID | Chemical Structure | IC$_{50}$(µM) |
|----|---|---|
| 47 | 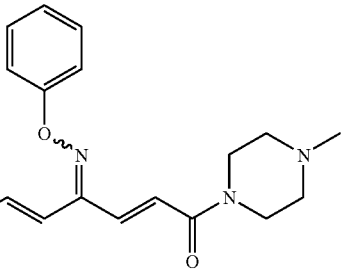 | 8.73 |
| 48 | 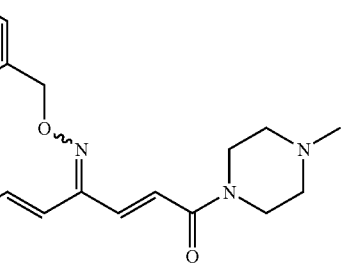 | 23.36 |
| 49 | 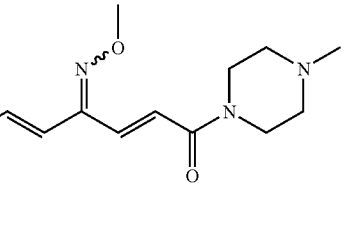 | >1000 |
| 50 | 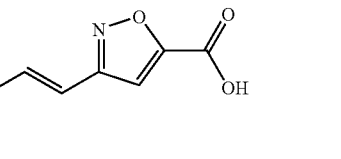 | >1000 |
| 51 | 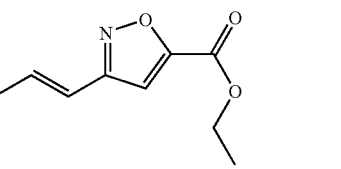 | 533.2 |
| 52 | 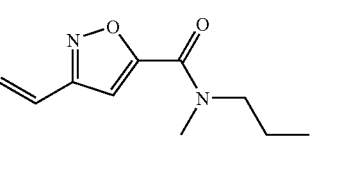 | 194.6 |

Obviously, numerous modifications and variations of the present invention are possible in light of the above teachings. It is therefore to be understood that within the scope of the appended claims, the invention may be practiced otherwise than as specifically described herein.

We claim:

1. A compound or pharmaceutically acceptable salt thereof having the formula (I)

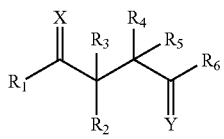

(I)

wherein $R_1$, $R_2$, $R_3$, $R_4$, $R_5$, and $R_6$ are independently a hydrogen atom or an alkyl, alkenyl, alkynyl, or aryl comprising 1 to 30 carbon atoms and which is unsubstituted or substituted by at least one of hydroxy, cyano, mercapto, halogen, —$OR_7$, $SR_7$, —$NR_7R_8$, —$CONR_7R_8$, or —$OCONR_7R_8$, wherein $R_7$ and $R_8$ are a hydrogen atom; an alkyl, alkenyl, or alkynyl comprising 1 to 20 carbon atoms; a cyclic or heterocyclic group comprising 5 or 6 ring atoms of which from 0 to 3 are nitrogen and/or oxygen and/or sulphur hetero-atoms, said cyclic or heterocyclic group being unsubstituted or substituted by at least one of hydroxy, cyano, mercapto, halogen, or an alkyl group comprising 1 to 6 carbon atoms; and X and Y are respectively O, $NR_7$ or S, wherein when X and Y are O, and if $R_2$, $R_4$ are hydrogen, $R_1$-$R_3$ or both $R_1$-$R_3$ and $R_5$-$R_6$ form a cyclic or an acyclic alkenyl; when X and Y are O, and if $R_2$, $R_4$ form a single bond, $R_1$ is

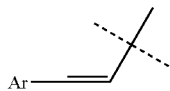

wherein Ar is an aryl or heteroaryl.

2. The compound of claim 1, wherein X and Y are O, and $R_6$ is —$NR_7R_8$.

3. The compound of claim 1, wherein X and Y are O.

4. The compound of claim 1, wherein the compound has the following formula:

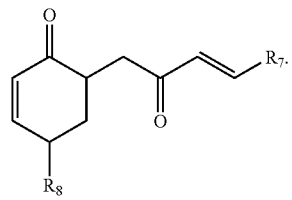

5. The compound of claim 4, wherein $R_7$ and $R_8$ are $C_1$-$C_{10}$ alkyl and $C_6$-$C_{10}$ aryl, respectively.

6. The compound of claim 1, wherein the compound has the following formula:

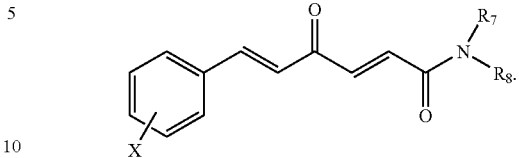

7. The compound of claim 6, wherein $R_7$ and $R_8$ are $C_1$-$C_{10}$ alkyl and $C_6$-$C_{10}$ aryl, respectively.

8. The compound of claim 7, wherein X is H, 3-OMe, 4-OMe, or 3,4-di-OMe.

9. A pharmaceutical composition comprising the compound of claim 1 and a pharmaceutically acceptable carrier.

10. The pharmaceutical composition of claim 9, wherein the composition is suitable for delivery via routes of administration selected from the group consisting of oral and parenteral administration.

11. The pharmaceutical composition of claim 10, wherein said composition is suitable for oral delivery and further comprises one or more ingredients selected from the group consisting of a diluent, an edible carrier, a binder, an excipient, a disintegrating agent, a lubricant, a glidant, and a sweetening agent.

12. The pharmaceutical composition of claim 10, wherein said composition is suitable for parenteral delivery and comprises one or more ingredients selected from the group consisting of a sterile diluent, antimicrobial agents, antioxidants, buffers, and tonicity adjusting agents.

13. A pharmaceutical composition comprising the compound of claim 2 and a pharmaceutically acceptable carrier.

14. The pharmaceutical composition of claim 13, wherein the composition is suitable for delivery via routes of administration selected from the group consisting of oral, parenteral, intravenous, and combinations thereof.

15. The pharmaceutical composition of claim 14, wherein said composition is suitable for oral delivery and further comprises one or more ingredients selected from the group consisting of a diluent, an edible carrier, a binder, an excipient, a disintegrating agent, a lubricant, a glidant, and a sweetening agent.

16. The pharmaceutical composition of claim 14, wherein said composition is suitable for parenteral delivery and comprises one or more ingredients selected from the group consisting of a sterile diluent, antimicrobial agents, antioxidants, buffers, and tonicity adjusting agents.

17. A pharmaceutical composition comprising the compound of claim 3 and a pharmaceutically acceptable carrier.

18. The pharmaceutical composition of claim 17, wherein the composition is suitable for delivery via routes of administration selected from the group consisting of oral, parenteral, intravenous, and combinations thereof.

19. The pharmaceutical composition of claim 18, wherein said composition is suitable for oral delivery and further comprises one or more ingredients selected from the group consisting of a diluent, an edible carrier, a binder, an excipient, a disintegrating agent, a lubricant, a glidant, and a sweetening agent.

20. The pharmaceutical composition of claim 18, wherein said composition is suitable for parenteral delivery and comprises one or more ingredients selected from the group consisting of a sterile diluent, antimicrobial agents, antioxidants, buffers, and tonicity adjusting agents.

21. A pharmaceutical composition comprising the compound of claim 4 and a pharmaceutically acceptable carrier.

22. The pharmaceutical composition of claim 21, wherein the composition is suitable for delivery via routes of administration selected from the group consisting of oral and parenteral administration.

23. The pharmaceutical composition of claim 22, wherein said composition is suitable for oral delivery and further comprises one or more ingredients selected from the group consisting of a diluent, an edible carrier, a binder, an excipient, a disintegrating agent, a lubricant, a glidant, and a sweetening agent.

24. The pharmaceutical composition of claim 22, wherein said composition is suitable for parenteral delivery and comprises one or more ingredients selected from the group consisting of a sterile diluent, antimicrobial agents, antioxidants, buffers, and tonicity adjusting agents.

25. A pharmaceutical composition comprising the compound of claim 5 and a pharmaceutically acceptable carrier.

26. The pharmaceutical composition of claim 25, wherein the composition is suitable for delivery via routes of administration selected from the group consisting of oral and parenteral administration.

27. The pharmaceutical composition of claim 26, wherein said composition is suitable for oral delivery and further comprises one or more ingredients selected from the group consisting of a diluent, an edible carrier, a binder, an excipient, a disintegrating agent, a lubricant, a glidant, and a sweetening agent.

28. The pharmaceutical composition of claim 26, wherein said composition is suitable for parenteral delivery and comprises one or more ingredients selected from the group consisting of a sterile diluent, antimicrobial agents, antioxidants, buffers, and tonicity adjusting agents.

29. A pharmaceutical composition comprising the compound of claim 6 and a pharmaceutically acceptable carrier.

30. The pharmaceutical composition of claim 29, wherein the composition is suitable for delivery via routes of administration selected from the group consisting of oral and parenteral administration.

31. The pharmaceutical composition of claim 30, wherein said composition is suitable for oral delivery and further comprises one or more ingredients selected from the group consisting of a diluent, an edible carrier, a binder, an excipient, a disintegrating agent, a lubricant, a glidant, and a sweetening agent.

32. The pharmaceutical composition of claim 30, wherein said composition is suitable for parenteral delivery and comprises one or more ingredients selected from the group consisting of a sterile diluent, antimicrobial agents, antioxidants, buffers, and tonicity adjusting agents.

33. A pharmaceutical composition comprising the compound of claim 7 and a pharmaceutically acceptable carrier.

34. The pharmaceutical composition of claim 33, wherein the composition is suitable for delivery via routes of administration selected from the group consisting of oral, and parenteral administration.

35. The pharmaceutical composition of claim 34, wherein said composition is suitable for oral delivery and further comprises one or more ingredients selected from the group consisting of a diluent, an edible carrier, a binder, an excipient, a disintegrating agent, a lubricant, a glidant, and a sweetening agent.

36. The pharmaceutical composition of claim 34, wherein said composition is suitable for parenteral delivery and comprises one or more ingredients selected from the group consisting of a sterile diluent, antimicrobial agents, antioxidants, buffers, tonicity and adjusting agents.

37. A pharmaceutical composition comprising the compound of claim 8 and a pharmaceutically acceptable carrier.

38. The pharmaceutical composition of claim 37, wherein the composition is suitable for delivery via routes of administration selected from the group consisting of oral and parenteral administration.

39. The pharmaceutical composition of claim 38, wherein said composition is suitable for oral delivery and further comprises one or more ingredients selected from the group consisting of a diluent, an edible carrier, a binder, an excipient, a disintegrating agent, a lubricant, a glidant, and a sweetening agent.

40. The pharmaceutical composition of claim 38, wherein said composition is suitable for parenteral delivery and comprises one or more ingredients selected from the group consisting of a sterile diluent, antimicrobial agents, antioxidants, buffers, tonicity and adjusting agents.

41. The compound of claim 8, wherein X is H.

42. The compound of claim 8 wherein X is 3-OMe.

43. The compound of claim 8 wherein X is 4-OMe.

44. The compound of claim 8 wherein X is 3, 4-di-OMe.

45. A pharmaceutical composition comprising the compound of claim 41 and a pharmaceutically acceptable carrier.

46. The pharmaceutical composition of claim 45, wherein the composition is suitable for delivery via routes of administration selected from the group consisting of oral and parenteral administration.

47. The pharmaceutical composition of claim 46, wherein said composition is suitable for oral delivery and further comprises one or more ingredients selected from the group consisting of a diluent, an edible carrier, a binder, an excipient, a disintegrating agent, a lubricant, a glidant, and a sweetening agent.

48. The pharmaceutical composition of claim 46, wherein said composition is suitable for parenteral delivery and comprises one or more ingredients selected from the group consisting of a sterile diluent, antimicrobial agents, antioxidants, buffers, tonicity and adjusting agents.

49. A pharmaceutical composition comprising the compound of claim 42 and a pharmaceutically acceptable carrier.

50. The pharmaceutical composition of claim 49, wherein the composition is suitable for delivery via routes of administration selected from the group consisting of oral and parenteral administration.

51. The pharmaceutical composition of claim 50, wherein said composition is suitable for oral delivery and further comprises one or more ingredients selected from the group consisting of a diluent, an edible carrier, a binder, an excipient, a disintegrating agent, a lubricant, a glidant, and a sweetening agent.

52. The pharmaceutical composition of claim 50, wherein said composition is suitable for parenteral delivery and comprises one or more ingredients selected from the group consisting of a sterile diluent, antimicrobial agents, antioxidants, buffers, tonicity and adjusting agents.

53. A pharmaceutical composition comprising the compound of claim 43 and a pharmaceutically acceptable carrier.

54. The pharmaceutical composition of claim 53, wherein the composition is suitable for delivery via routes of administration selected from the group consisting of oral and parenteral administration.

55. The pharmaceutical composition of claim 54, wherein said composition is suitable for oral delivery and further comprises one or more ingredients selected from the group consisting of a diluent, an edible carrier, a binder, an excipient, a disintegrating agent, a lubricant, a glidant, and a sweetening agent.

56. The pharmaceutical composition of claim 54, wherein said composition is suitable for parenteral delivery and comprises one or more ingredients selected from the group consisting of a sterile diluent, antimicrobial agents, antioxidants, buffers, tonicity and adjusting agents.

57. A pharmaceutical composition comprising the compound of claim 44 and a pharmaceutically acceptable carrier.

58. The pharmaceutical composition of claim 57, wherein the composition is suitable for delivery via routes of administration selected from the group consisting of oral and parenteral administration.

59. The pharmaceutical composition of claim 58, wherein said composition is suitable for oral delivery and further comprises one or more ingredients selected from the group consisting of a diluent, an edible carrier, a binder, an excipient, a disintegrating agent, a lubricant, a glidant, and a sweetening agent.

60. The pharmaceutical composition of claim 58, wherein said composition is suitable for parenteral delivery and comprises one or more ingredients selected from the group consisting of a sterile diluent, antimicrobial agents, antioxidants, buffers, tonicity and adjusting agents.

\* \* \* \* \*